United States Patent [19]

Eggler et al.

[11] Patent Number: 4,642,373

[45] Date of Patent: Feb. 10, 1987

[54] SUBSTITUTED DODECAHYDROTRIPHEYLENES, AND DECAHYDROPYRROLO[1,2-F]PHENAN-THRIDINES AS CNS AGENTS

[75] Inventors: James F. Eggler, Stonington; Michael R. Johnson, Gales Ferry; Lawrence S. Melvin, Jr., Ledyard, all of Conn.

[73] Assignee: Pfizer Inc., New York, N.Y.

[21] Appl. No.: 628,543

[22] Filed: Jul. 6, 1984

Related U.S. Application Data

[62] Division of Ser. No. 358,765, Mar. 16, 1982, Pat. No. 4,473,704.

[51] Int. Cl.$^4$ .................................... C07C 69/616
[52] U.S. Cl. ........................... 560/139; 544/125; 544/154; 544/360; 544/380; 546/71; 546/195; 546/200; 546/272; 546/285; 548/518; 548/528; 560/108; 564/97; 564/222; 568/326; 568/714; 568/732
[58] Field of Search ............... 560/139, 108; 568/326; 544/154, 380; 546/195, 285; 548/528; 544/360

[56] References Cited

U.S. PATENT DOCUMENTS

| | | | |
|---|---|---|---|
| 4,087,545 | 5/1978 | Archer et al. | 514/454 |
| 4,152,450 | 5/1979 | Day et al. | 514/454 |
| 4,228,169 | 10/1980 | Johnson et al. | 546/108 X |
| 4,309,545 | 1/1982 | Johnson | 546/108 |

Primary Examiner—Natalie Trousof
Assistant Examiner—Patricia M. Scott
Attorney, Agent, or Firm—Charles J. Knuth; Peter C. Richardson; Mark Dryer

[57] ABSTRACT 1,2,3,4,4a,4b,5,6,7,8,8a,12b-Dodecahydro-7-(oxo, hydroxy or amino)-9-hydroxy-11-(alkyl, alkoxy or alkoxyalkyl)triphenylenes, 2,3,3a,3b,4,5,6,7,7a,11b-decahydro-6-(oxo, hydroxy or amino)-8-hydroxy-10-(alkyl, alkoxy or alkoxyalkyl)-1H-cyclopenta[1]-phenanthrenes, 2,3,4,4a,4b,5,6,7,8,8a-decahydro-7-(oxo, hydroxy or amino)-9-hydroxy-11-(alkyl, alkoxy, alkoxyalkyl, aralkyl, aralkoxy, aryloxyalkyl or aralkoxyalkyl)-1H-pyrido[1,2-f]phenanthridines, and 1,2,3,3a,3b,4,5,6,7,7a-decahydro-6-(oxo, hydroxy or amino)-8-hydroxy-10-(alkyl, alkoxy or alkoxyalkyl)pyrrolo[1,2-f]phenanthridines and derivatives are valuable as central nervous system active agents or as intermediates to compounds having such activity.

7 Claims, No Drawings

SUBSTITUTED DODECAHYDROTRIPHEYLENES, AND DECAHYDROPYRROLO[1,2-F]PHENANTHRIDINES AS CNS AGENTS

This is a division of application Ser. No. 358,765, filed on Mar. 16, 1982, now U.S. Pat. No. 4,473,704, issued Sept. 25, 1984.

BACKGROUND OF THE INVENTION

This invention relates to novel compounds which are substituted dodecahydrotriphenylenes, decahydro-1H-cyclopenta[1]phenanthrenes, decahydro-1H-pyrido[1,2-f]phenanthridines and decahydropyrrolo[1,2-f]phenanthridines and which are useful in mammals, including man, as CNS agents, especially as analgesics, tranquilizers, and antiemetics, as antidiarreals, as antitussives, as diuretics and as agents for the treatment of glaucoma; and as intermediates therefor.

Despite the current availability of a number of analgesic agents, the search for new and improved agents continues, thus pointing to the lack of an agent useful for the control of broad levels of pain and accompanied by a minimum of side-effects. The most commonly used agent, aspirin, is of no practical value for the control of severe pain and is known to exhibit various undesirable side-effects. Other, more potent analgesic agents such as d-propoxyphene, codeine, and morphine, possess addictive liability. The need for improved and potent analgesic agents is, therefore, evident.

There is also a continuing need for potent antiemetic agents having minimal side-effects, particularly in patients receiving cancer chemotherapy.

The analgesic properties of 9-nor-9beta-hydroxyhexahydrocannabinol and related compounds have been reported by Wilson and May, J. Med. Chem. 17, 475–476 (1974); 18, 700–703 (1975). The antiemetic activity of delta⁹-tetrahydrocannabinol in patients undergoing cancer chemotherapy has been reported by Sallan et al. New England J. Med. 293, 795 (1975).

Various 5,6,6a,7,8,9,10,10a-octahydro-9-(oxo or hydroxy)-1-hydroxy-3-(alkyl, alkoxy, alkoxyalkyl, aralkyl, aralkoxy, aralkoxyalkyl, or aryloxyalkyl)phenanthridine derivatives have been reported to possess various medicinal properties particularly, analgesic activity, Johnson, U.S. Pat. No. 4,260,764, as well as antiemetic activity, Johnson and Milne, U.S. Pat. No. 4,228,169, Nov. 14, 1980.

Various 1,2,3,4,4a,9,10,10a-octahydro-3-(oxo or hydroxy)-5-hydroxy-7-(alkyl, alkoxy, alkoxyalkyl, aralkyl, aralkoxy, aralkoxyalkyl, or aryloxy)phenanthrenes are also reported to possess analgesic activity, Althuis et al., U.S. Pat. No. 4,188,495 (Feb. 12, 1980).

Various 6a,7,8,9,10,10a-hexahydro-9-amino-1-hydroxy-3-alkyl-6H-benzo[c]chromene derivatives are reported to be useful as analgesics, antidepressants, antianxiety, and hypotensive agents, Day et al., U.S. Pat. No. 4,152,450 (May 1, 1979); while various 7,8,10,10a-tetrahydro-1-hydroxy-3-alkyl-6H,6aH-benzo[c]chromen-9-one derivatives are reported as antiemetic drugs, Archer et al., U.S. Pat. No. 4,087,545 (May 2, 1978), and earlier as having antidepressant, analgesic and antianxiety properties, Archer, U.S. Pat. Nos. 3,953,603 (Apr. 27, 1976), 3,944,673 (Mar. 16, 1976) and 3,928,598 (Dec. 23, 1975).

Johnson, U.S. Pat. No. 4,309,545 (Jan. 5, 1982) discloses 5,6,6a,7,8,9,10,10a-octahydro-9-amino-1-hydroxy-3-(alkyl, alkoxy, alkoxyalkyl, aralkyl, aralkoxy, aralkoxyalkyl or aryloxyalkyl)phenanthridine derivatives as having CNS activity, particularly useful as analgesics and antiemetics.

U.S. Pat. No. 4,476,131 and its divisional U.S. Pat. No. 4,576,964 disclose various 1,2,3,4,4a,9,10,10a-octahydro-9-(substituted)-8-hydroxy-6-(alkyl, alkoxy, alkoxyalkyl, aralkyl, aralkoxy, aralkoxyalkyl or aryloxyalkyl)phenanthrene, 2,3,3a,4,5,9b-hexahydro-5-(substituted)-6-hydroxy-8-(alkyl, alkoxy, alkoxyalkyl, aralkyl, aralkoxy, aralkoxyalkyl or aryloxyalkyl)cyclopenta[a]naphthalene, 2,3,4,4a,5,6-hexahydro-6-(substituted)-7-hydroxy-9-(alkyl, alkoxy, alkoxyalkyl, aralkyl, aralkoxy, aralkoxyalkyl or aryloxyalkyl)-1H-pyrido[1,2-a]quinoline and 1,2,3,3a,4,5-hexahydro-5-(substituted)-6-hydroxy-8-(alkyl, alkoxy, alkoxyalkyl, aralkyl, aralkoxy, aralkoxyalkyl or aryloxyalkyl)pyrrolo[1,2-a]quinoline derivatives having similar CNS activity.

The nomenclature employed herein is based on Rigaudy and Klesney, I.U.P.A.C. Nomenclature of Organic Chemistry—1979 Edition, Permangon Press, New York, including the use of R and S to designate absolute stereochemistry and R* and S* to designate relative stereochemistry. Formulae showing dotted and heavy bonds are generally intended to specify relative stereochemistry, unless otherwise specified in the text.

SUMMARY OF THE INVENTION

Compounds of the present invention having pharmaceutical utility are of the formulae

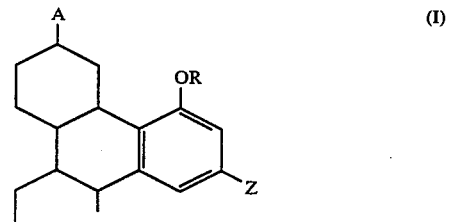

and

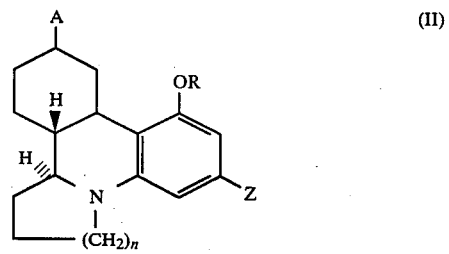

wherein n is 1 or 2;

A is OH, ($C_1$–$C_5$)alkanoyloxy, ($C_1$–$C_5$)alkanoylamino or ($C_1$–$C_4$)alkanesulfonamido;

R is H, benzoyl, ($C_1$–$C_5$)alkanoyl or —CO(CH$_2$)$_m$Y, wherein m is 1, 2, 3 or 4, Y is —COOH, or —NR'R", R' and R" when taken separately are each independently H or ($C_1$–$C_4$)alkyl, and R' and R" when taken together with the nitrogen to which they are attached are piperidino, pyrrolo, pyrrolidino, morpholino or N-[($C_1$–$C_4$)alkyl]piperazino; and Z is ($C_5$-$C_{13}$)alkyl, ($C_5$-$C_{13}$)alkoxy, ($C_5$-$C_{13}$)alkoxyalkyl, ($C_8$-$C_{13}$)pyridylalkyl, ($C_8$-$C_{13}$)pyridylalkoxy, ($C_8$-$C_{13}$)pyridyloxyalkyl, ($C_8$-$C_{13}$)pyridylalkoxyalkyl, ($C_9$-$C_{14}$)phenylalkyl, ($C_9$-$C_{14}$)phenylalkoxy, ($C_9$-$C_{14}$)phenoxyalkyl, or ($C_9$-$C_{14}$)phenylalkoxyalkyl, wherein said phenyl groups are optionally substituted with a chloro or a fluoro.

Here and elsewhere in this application, the bracketed ranges of carbon atoms are intended to encompass the range of carbon atoms of the entire group which follows. For example ($C_1$-$C_5$)alkanoyl encompasses HCO— to $C_4H_9$CO—, while ($C_9$-$C_{14}$)phenylalkyl encompasses ($C_6H_5$)$C_3H_6$— to ($C_6H_5$)$C_8H_{16}$—.

Compounds of the present invention having particular utility as intermediates, in addition to pharmaceutical utility, are of the formulae

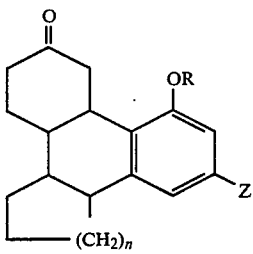

(III)

and

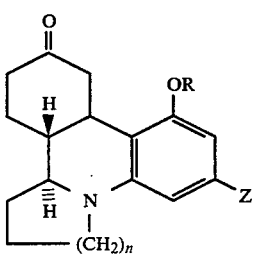

(IV)

wherein n, R and z are as defined above.

Also encompassed by the present invention are pharmaceutically-acceptable acid addition salts of compounds of the formulae (II) and (IV), and of the formulae (I) and (III) wherein R is —CO($CH_2$)$_m$Y and Y is —NR'R", as well as the pharmaceutically-acceptable cationic salts of compounds of the formulae (I) to (IV) wherein R is —CO($CH_2$)Y and Y is —COOH.

The numbering and ring systems for the compounds of the present invention are as follows:

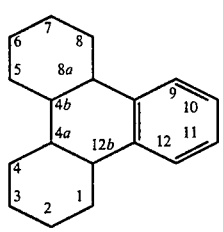

triphenylenes

-continued

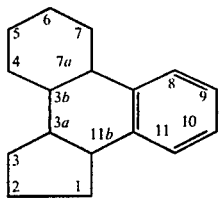

1H—cyclopenta[l]-phenanthrenes

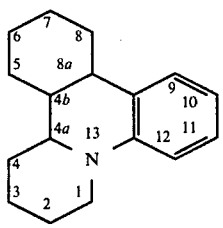

1H—pyrido[1,2-f]-phenanthridines

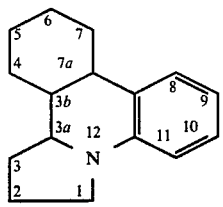

pyrrolo[1,2-f]-phenanthridines

Thus the compounds of the formulae (I) to (IV) are named as follows:

(I), n=1: 2,3,3a,3b,4,5,6,7,7a,11b-decahydro-6-(A-substituent)-8-(OR-substituent)-10-(Z-substituent)-1H-cyclopenta[l]phenanthrene;

(III), n=1: 3,3a,3b,4,5,7,7a,11b-octahydro-8-(OR-substituent)-10-(Z-substituent)-1H,2H-cyclopenta[l]phenanthren-6-one;

(I), n=2: 1,2,3,4,4a,4b,5,6,7,8,8a,12b-dodecahydro-7-(A-substituent)-9-(OR-substituent)-11-(Z-substituent)triphenylene;

(III), n=2: 2,3,4,4a,4b,5,6,8,8a,12b-decahydro-9-(OR-substituent)-11-(Z-substituent)-1H-triphenylen-7-one;

(II), n=1: 1,2,3,3aS*,3bR*,4,5,6,7,7a-decahydro-6-(A-substituent)-8-(OR-substituent)-10-(Z-substituent)pyrrolo[1,2-f]phenanthridine;

(IV), n=1: 2,3,3aS*,3bR*,4,5,7,7a-octahydro-8-(OR-substituent)-10-(Z-substituent)-1H-pyrrolo[1,2-f]phenanthridin-6-one;

(II), n=2: 2,3,4,4aS*,4bR*,5,6,7,8,8a-decahydro-7-(A-substituent)-9-(OR-substituent)-11-(Z-substituent)-1H-pyrido[1,2-f]phenanthridine; and (IV), n=2: 3,4,4aS*,4bR*, 5,6,8,8a-octahydro-9-(OR-substituent)-11-(Z-substituent)-1H,2H-pyrido[1,2-f]phenanthridin-7-one.

Compounds of the present invention useful as intermediates are of the formulae

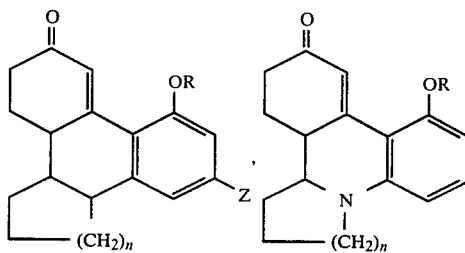
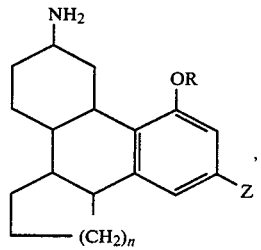
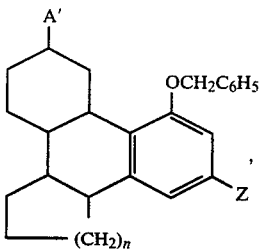
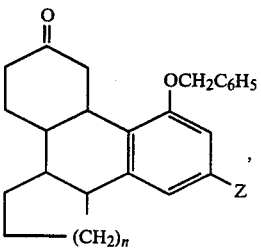
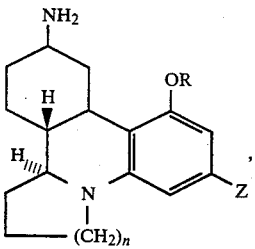
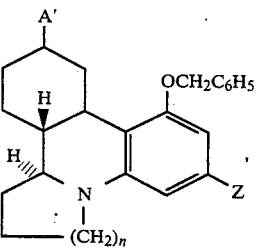

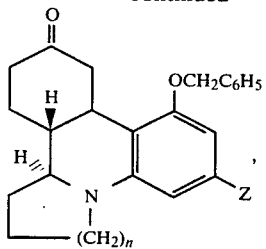

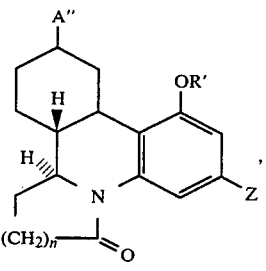

wherein
n, R and Z are as defined above;
A' is OH, (C$_1$–C$_5$)alkanoyloxy, NH$_2$, (C$_1$–C$_5$)alkanoylamino or (C$_1$–C$_4$)alkanesulfonamido;
A" is OH or NH$_2$; and
R' is H, benzoyl or (C$_1$–C$_5$)alkanoyl.

The compounds (V) to (XI) are named by analogy to the compounds (I) to (IV). For example, the compounds of the formula (XI) when n=1, are named as follows:

3,3aS*,3bR*,4,5,6,7,7a-hexahydro-6-(A"-substituent)-8-(OR'-substituent)-10-(Z-substituent)-2H-pyrrolo[1,2-f]phenanthridin-1-one.

The preferred relative stereochemistry for the compounds (I), (III), (V), (VI) and (VII) is 3aS*,3bS*-/4aS*,4bS*, i.e. 3a,3b/4a,4b trans. Within these groups, the more preferred stereochemistry is 3aS*,11bR*-/4aS*,12bR*, i.e. 3a,11b/4a,12b also trans. Within the latter group, even more preferred are compounds having 3bS*,7aR*/4bS*,8aR*, i.e. 3b,7a/4b,8a also trans. Finally, in those compounds of the last named group having a substituent A or A', said substituent is preferably equatorial (6R*/7R*), i.e. the group A or A' on the opposite side of the molecule from the 7a/8a-hydrogen. In the corresponding compounds which are optically active, the same considerations of relative stereochemistry apply, with the most highly preferred compounds having the 7aR/8aR configuration, e.g.,

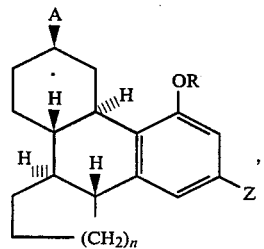

named (when n=2) as follows:
1,2,3,4,4aS,4bS,5,6,7R,8,8aR,12bR-dodecahydro-7-(A-substituent)-9-(OR-substituent)-11-(Z-substituent)-triphenylene.

The compounds of the formulae (II), (IV), (VIII), (IX), (X) and (XI) have relative stereochemistry specified as 3aS*,3bR*/4aS*,4bR*, i.e. 3a,3b/4a,4b-trans. Further preferred relative stereochemistry in all of these cases is 3bR*,7aR*/4bR*,8aR*, i.e. 3b,7a/4b,8a-trans. Within these groups of compounds which have a substituent A, A' or A", said substituent is preferably equatorial (6R*/7R*), i.e. on the opposite side of the molecule from the 7a/8a-hydrogen. In the corresponding compounds, which are optically active, the same considerations of relative stereochemistry apply, with the most highly preferred compounds having the 7aR/8aR configuration, e.g.,

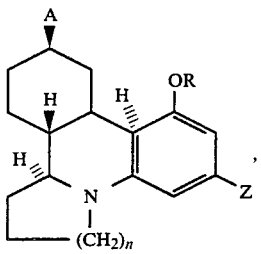

(XIII)

named (when n=2) as follows:
2,3,4,4aS,4bR,5,6,7R,8,8aR-decahydro-7-(A-substituent)-9-(OR-substituent)-11-(Z-substituent)-1H-pyrido[1,2-f]phenanthridine.

In all cases, the preferred value of Z is 5-phenyl-2-pentyloxy; 5-phenyl-2R-pentyloxy, i.e.,

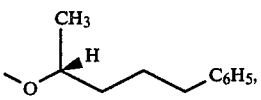

(XIV)

is most preferred. The preferred value of R is acetyl and that of A is hydroxy. The preferred value of n is 2.

Also encompassed by the present invention are oral and parenteral formulations of compounds of the formulae (I), (II), (III) and (IV), as well as methods of alleviating pain (analgesia) and preventing emesis in mammals, including man.

DETAILED DESCRIPTION OF THE INVENTION

Compounds of the formulae (I) and (II), wherein A is OH, are prepared by sodium borohydride reduction of corresponding compounds of the formulae (III) and (IV). It is preferred that the phenolic groups of the latter compounds be protected by an acyl group, i.e., R other than hydrogen. The reduction is generally carried out in a lower alkanol (e.g., methanol, ethanol, isopropanol) within the temperature range −15° to 35° C., preferably −5° to 15° C. when ethanol is the solvent, preferably below −35° C. when methanol is the solvent, with at least one equivalent of sodium borohydride. Reaction time is not critical. For example at a 1% substrate concentration in ethanol, with a substantial excess of hydride, the reaction is essentially complete within 10 minutes at 0° C. By the same method, precursor compounds of the formulae (VII) and (X) are converted to the corresponding compounds of the formulae (VI) and (IX) wherein A' is hydroxy, and precursor compounds of the formula

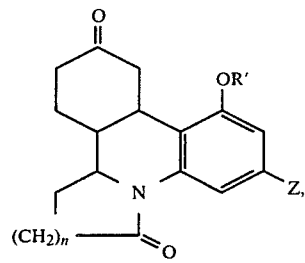

(XV)

wherein n, R' and Z are as defined above, are reduced to compounds of the formula (XI). Alternatively the various ketone reductions of this paragraph are carried out by hydrogenation over a noble metal catalyst. Pressure is not critical, although, from the viewpoint of equipment cost, pressures from ambient to about 7 kg./cm.$^2$ are preferred. Temperature is likewise not critical, the range 0°–50° C. is preferred, ambient temperature being most preferred from the viewpoint of cost. Solvent is not critical; any solvent which does not react with reactants, products, or reagents to significantly reduce yield (i.e. reaction inert) being well suited; lower alkanols are particularly well suited for this purpose. The noble metal catalyst can be of the unsupported type (e.g. Pt black, PtO$_2$, PdCl$_2$, RhCl$_3$) or of the supported type (e.g. Rh/C, Pd/BaSO$_4$). The most highly preferred catalyst is Pd/C usually 1–10% Pd by weight. The hydrogenation is carried out until substantially one equivalent is taken up. When the substrate contains a benzyl group [compounds of the formulae (VII) and (X)], this method is not preferred if retention of the benzyl group is desired. However, by permitting the latter compounds to take up two equivalents of hydrogen under these conditions the alcoholic compounds of the formulae (I) and (II), wherein A is hydroxy and R is H, are formed directly, representing an alternative synthesis of these compounds. By either the hydride or catalytic hydrogenation methods of this paragraph, both isomeric alcohols are produced, but the equatorial alcohol predominates, especially under the preferred hydrogenation conditions.

The ketones of the formulae (III), (IV), (VII), (X) and (XV) are derived from the corresponding alpha,beta-unsaturated ketones, of the partial formula

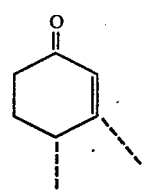

(XVI)

by Li/NH$_3$ reduction. If desired, the reduction is carried out in the presence of a reaction-inert diluent (as defined above) such as an ether, conveniently tetrahydrofuran. A slight excess of lithium metal is employed, determined by adding lithium portionwise until a blue color persists for several minutes. The reaction is carried out cold, e.g. −20° to −50° C., preferably at or below the boiling point of the reaction mixture so as to avoid the need for a pressure vessel. If the ketone derived by the present process has a free phenolic group, it can, if desired be acylated by any one of a number of methods standard to the organic chemist's art. Conveniently, at least one equivalent of an acylating agent (e.g. acetyl chloride, propionic anhydride, acetoformic acid reagent, benzoyl chloride, 3-dimethylaminopropionyl chloride hydrochloride, succinic anhydride, the mixed anhydride formed between benzoic acid and ethyl chloroformate, propyl chloroformate, etc.) is reacted with the phenolic ketone, usually in the presence of at least one equivalent of a tertiary organic amine (e.g. triethylamine, pyridine, 4-dimethylaminopyridine), and preferably an excess of said amine, in a reaction inert solvent (e.g. a chlorohydrocarbon such as methylene chloride) or in an excess of the amine (e.g. pyridine). When it is desired that the final product contain a phenolic acyl group and no alcoholic acyl group, it is preferred that the phenolic acyl group (if not already present) be introduced into compounds of the formulae (III) or (IV) at this stage of the overall process.

Alternatively, compounds of the formulae (I), (II) and (XI), wherein A or A″ is hydroxyl, are prepared by hydrogenation of the corresponding compounds of the partial formula (XVI), accomplishing the reduction of the double bond, the ketone group and (if present) the benzyl group in a single step. The conditions are as specified above for ketone hydrogenation, except that substantially two equivalents of hydrogen are consumed (three equivalents if a benzyl group is also present and reduced). Little of the 3b,7a/4b,8a-cis or 6/7-axial alcohol compounds are formed under these conditions, particularly when the preferred catalyst (Pd/C) is employed.

In a further synthetic method, phenols of the formulae (I) and (II), wherein R is hydrogen, are obtained by the hydrogenolysis of the corresponding benzyl ethers of the formulae (VI) and (IX).

In the specific case of the alcohols of the formula (II), wherein A is hydroxy and R is H, such compounds are also obtained by relatively vigorous hydride reduction of the corresponding compounds of the formula (XI), wherein A″ is hydroxy. If acyl groups are present on either the alcohol or phenol groups, they will be reductively removed under the conditions employed for the reduction of the lactam. Suitable conditions are excess lithium aluminum hydride at an elevated temperature (45°–85° C.) in a higher boiling ether such as tetrahydrofuran or dimethoxyethane. When the reflux temperature of the mixture is exceeded, a pressure vessel is employed. Refluxing tetrahydrofuran represents conditions well suited for this reaction.

If desired, alcohols of the formulae (I), (II), (VI) and (IX), wherein A or A′ is hydroxy, are acylated according to conditions detailed above, yielding the corresponding compounds of the formulae (I), (II), (VI) and (IX), wherein A or A′ is $(C_1-C_5)$alkanoyloxy. When the alcohols also contain a free phenolic group, the phenolic group is also acylated under these conditions, necessitating the use of at least two equivalents each of acylating agent and base, and yielding the bis-$(C_1-C_5)$alkanoates. The phenolic acyl group, if desired, is readily removed from these compounds by solvolysis in methanol in the presence of anhydrous potassium carbonate at reduced temperature ($-15°$ to $15°$ C.), yielding compounds of the formula (I) or (II) wherein A is $(C_1-C_5)$alkanoyloxy and R is hydrogen. The same compounds are alternatively obtained by hydrogenolysis of compounds of the formulae (VI) or (IX) wherein A′ is $(C_1-C_5)$alkanoyloxy, using conditions as described above.

If desired, compounds of the formulae (I) and (II), wherein A is $(C_1-C_5)$alkanoyloxy and R is hydrogen, are further acylated to produce the corresponding compounds of the formulae (I) and (II) wherein A is $(C_1-C_5)$ alkanoyloxy and R is other than hydrogen, using a method of acylation as detailed above. This route has particular value in the preparation of mixed esters.

Compounds of the formulae (I) and (II) wherein A is $(C_1-C_5)$alkanoylamino or $(C_1-C_4)$alkanesulfonamido are prepared by acylation of the corresponding compounds of the formulae (V) and (VIII). Conditions as described above for the acylation of hydroxy compounds can be used for this purpose. When R is H in the substrate (V) or (VIII), the phenolic hydroxyl group is also acylated. If desired, the phenolic acyl group is removed by selective hydrolysis as described above for bis-esters. Alternatively, compounds of the formulae (I) and (II) wherein A is amino and R is hydrogen are selectively acylated on the amine function by using no more than one equivalent of the acylating agent (e.g. isobutyryl chloride, acetic anhydride, ethanesulfonyl chloride) and no extraneous base. Compounds of formulae (VI) and (IX) wherein A′ is amino are likewise acylated to the corresponding compounds of the formulae (VI) and (IX) wherein A′ is $(C_1-C_5)$alkanolyamino or $(C_1-C_4)$alkanesulfonamido according to the various methods of this paragraph. Hydrogenolysis of the latter compounds, under the conditions and preferred conditions detailed above, with uptake of substantially one equivalent of hydrogen, provides an alternative route to compounds of the formulae (I) and (II) wherein A is $(C_1-C_5)$alkanoylamino or $(C_1-C_4)$alkanesulfonamido and R is H.

If desired, the last-named compounds are acylated on the phenolic hydroxyl group according to methods detailed above to yield corresponding compounds of the formulae (I) and (II) wherein A is $(C_1-C_5)$alkanoylamino or $(C_1-C_4)$alkanesulfonamido and R is other than H.

A number of methods are available for the synthesis of the precursor amines of the formulae (V), (VIII), and (XI) wherein A″ is amino. One route, particularly preferred for a compound already having a phenolic acyl group in place or when the desired compound is an axial amine, is the catalytic hydrogenation of the corresponding oxime of the partial formula

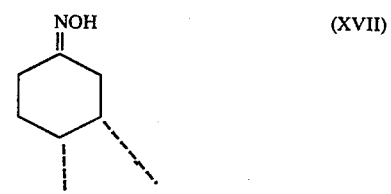

(XVII)

under the same conditions and preferred conditions of hydrogenation as those detailed above, in this case with the uptake of essentially two equivalents of hydrogen. The required oximes are derived from the corresponding ketones of the partial formula (XVI) using conditions well known in the chemical art. For example reaction of the ketone with hydroxylamine hydrochloride is carried out in an excess of a tertiary amine such as pyridine, optionally in the presence of a reaction inert solvent, such as a lower alkanol. Temperature is not critical (e.g. 25°–50° C.), ambient temperature being well suited for the purpose.

Alternatively, the amines of the formulae (V), (VIII) and (XI) wherein A″ is amino and R′ is hydrogen are prepared by hydride reduction of the corresponding methoxyimines of the partial formula

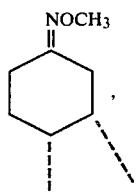 (XVIII)

Relatively vigorous conditions are required for this hydride reduction, such that if an acyl group is present on the phenolic hydroxylic group, said group will usually also be reductively removed. A well suited method is to react at least an equivalent sodium borohydride with the methoxyimino compound in tetrahydrofuran—initially at reduced temperature, but ultimately for up to several hours at reflux temperature. The methoxyimine is prepared according to methods detailed above for oximes, substituting methoxyamine for hydroxylamine.

Amines of the formulae (V) and (VIII) wherein R is hydrogen, as well as amides of the formulae (I) and (II) wherein A is $(C_1-C_5)$alkanoyloxy or $(C_1-C_4)$alkanesulfonamido and R is hydrogen are also prepared by hydrogenolysis of the corresponding benzyl ethers of the formulae (VII) and (IX) wherein A' is amino, $(C_1-C_5)$alkanoyloxy or $(C_1-C_4)$alkanesulfonamido according to methods detailed above for the debenzylation of related alcohols and esters. The precursors are derived from benzyl ketones via oxime or methoxyimine formation, reduction and acylation as detailed above.

Amines of the formula (VIII) wherein R is hydrogen are also obtained by the lithium aluminum hydride reduction of either the corresponding amines of the formula (XI) or of the corresponding methoxyimine precursors of the partial formula (XVIII), using at least the appropriate number of equivalents of lithium aluminum hydride and otherwise under conditions as detailed above for the reduction of hydroxy lactams. The required methoxyimine is derived by methods detailed above from the corresponding ketone of the formula (XV).

In all of the above cases which involve the reduction of an oxime or methoxyimine, the dominant product is the equatorial amine.

The following synthetic sequence is essentially common to the preparation of all of the tetracyclic alpha,-beta-unsaturated ketones of the partial formula (XVI) from the corresponding tricyclic ketones:

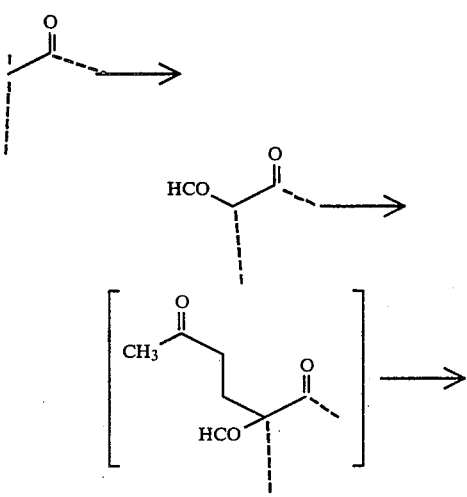 (XVI)

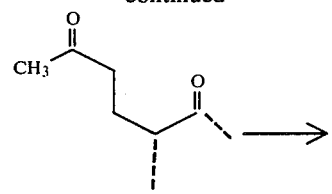

Typical conditions used for these transformations are detailed in the experimental section below. Typical tricyclic ketones used in this sequence are:

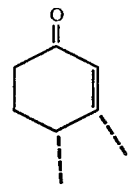  3,3aS*,4,9bR*-tetrahydro-6-hydroxy-8-(Z-substituent)-1H,2H—cyclopenta[a]naphthalen-5-one;

2,3,4,4aR*,10,10aS*-hexahydro-8-hydroxy-6-(Z-substituent)-1H—phenanthren-9-one;

2,3,4aS*,10,10aS*-hexahydro-8-hydroxy-6-(Z-substituent)-1H—phenanthren-9-one;

3,4,4a,5-tetrahydro-7-hydroxy-9-(Z-substituent)-1H,2H—pyrido[1,2-a]quinolin-6-one; and 3a,4-dihydro-6-hydroxy-8-(Z-substituent)-2H,3H—pyrrolo[1,2-a]quinoline-1,5-dione.

In the case of tricyclic nitrogen and 3a,9b/4a,10a-trans carbocyclic analogs, this reaction sequence results in tetracyclic compounds wherein the 3a,3b/4a,4b-hydrogens are trans, i.e., the 3b,4/4b,5-bond is pseudo-equatorial to the center ring. However, with 3a,9b/4a,10a-cis tricyclic analogs, there is no marked preference, and significant quantities of both the 3a,3b/4a,4b-cis and trans compounds are formed in this reaction sequence. When it is desired that the phenolic hydroxy group be substituted by benzyl or an acyl group (R as defined above, other than hydrogen), it is preferred that this group be introduced at the end of the sequence by methods described above and in specific examples hereinafter. When Z is other than alkoxy or aralkoxy, this group will generally be in place at the beginning of the sequence. When Z is alkoxy or aralkoxy, said group is generally formed from a phenolic group and an alkyl or aralkyl mesylate or halide, generally in the presence of at least one equivalent of base. This alkylation can be carried out at any stage of the reaction sequence under discussion, provided that it is carried out before any acylation or benzylation of the other phenolic group. It is preferred however, to have the complete group Z in place prior to entering this reaction sequence.

Depending on structure, various methods are available for preparation of the tricyclic ketones used as starting materials for the synthetic sequence of the preceding paragraph.

One sequence available for the preparation of numerous tricyclic carbon analogs employs as a first stage the heating of cyclohexanone or cyclopentanone with a suitable substituted phenyl Grignard in a high boiling, reaction inert solvent to produce a compound of the formula

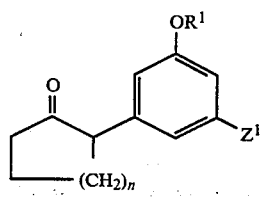

wherein n is as defined above, $R^1$ is methyl or benzyl and $Z^1$ is methoxy, benzyloxy, ($C_5$-$C_{13}$)alkyl, ($C_5$-$C_{13}$)alkoxyalkyl, ($C_9$-$C_{14}$)phenylalkyl, or ($C_9$-$C_{14}$)-phenylalkoxyalkyl. Condensation with alkyl acetate, dehydration, and hydrolysis of intermediate ester produces unsaturated acids of the formulae

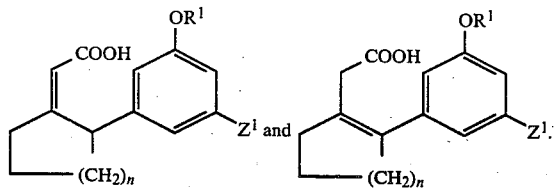

Equivalents such as malonate (decarboxylate to the acetate after hydrolysis) can be substituted for the alkyl acetate. Lithium in liquid ammonia reduction of the former yields the trans-form of the substituted acetic acid derivatives, while catalytic hydrogenation of the latter under conditions detailed above yields the cis-form of the acetic acid (with simultaneous debenzylation when $R^1$ is benzyl). Finally, cyclization, debenzylation or O-demethylation and alkylation when Z is a phenolic ether derivative, yields tricyclic ketones of the respective formulae

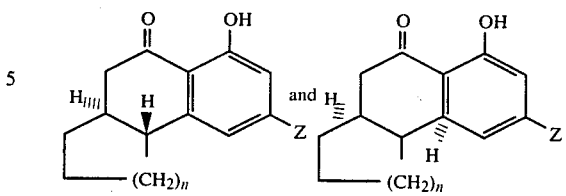

wherein n and Z are as hereinbefore defined.

Alternatively, suitable substituted aromatic aldehydes are condensed with nitromethane to yield trans-1-(disubstituted phenyl)-2-nitroethylenes of the formula

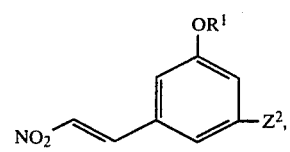

wherein $R^1$ is as defined above and $Z^2$ is methoxy, benzyloxy or Z is as defined above. Condensation of the latter with butadiene under Diehls-Alder conditions yields the corresponding 4-(substituted phenyl)-5-nitrocyclohexene. The Nef reaction converts the nitro compound to the unsaturated cyclohexanone derivative, viz, 6-(disubstituted phenyl)-3-cyclohexen-1-one which is hydrogenated according to methods detailed above (with simultaneous removal of benzyl, if present); demethylated if methyl ether is present (with simultaneous dealkylation if $Z^2$ is an alkoxy derivative); and alkylated if Z is an alkoxy derivative to yield a ketone of the formula

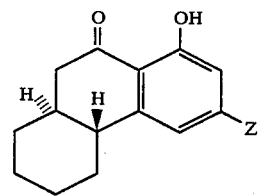

wherein Z is as defined above. It will be noted that inversion occurs in such alkylation reactions, e.g., 5-phenyl-2S-pentyl mesylate yields Z as 5-phenyl-2R-pentyloxy.

Corresponding tricyclic nitrogen analogs are conveniently prepared from 3,omega-dihalo acids and disubstituted anilines, e.g.,

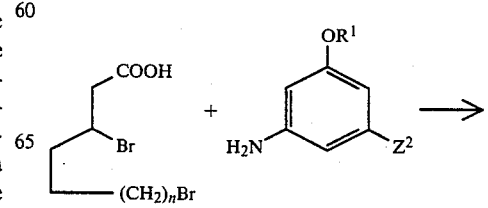

-continued

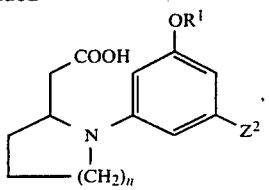

wherein n, $R^1$ and $Z^2$ are as defined above, followed by cyclization, debenzylation or demethylation (accompanied by dealkylation when $Z^2$ is an alkoxy derivative) and alkylation when Z is an alkoxy derivative to yield pyrrolo/pyrido[1,2-a]quinolinones of the formula

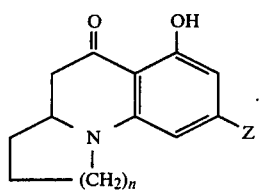

The corresponding tricyclic lactams are prepared from the same anilines by either initial alkylationcyclization with 3-halo diesters or reductive alkylation-cyclization with 3-keto diesters to yield intermediate esters which are hydrolyzed to acids of the formula

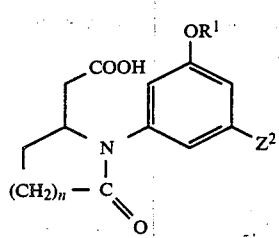

wherein n, $R^1$ and $Z^2$ are as defined above, followed by the further steps of the preceding paragraph to yield pyrrolo/pyrido[1,2-a]quinoline diones of the formula

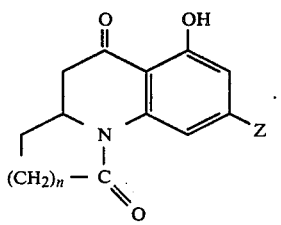

Many of the anilines, aromatic halides or aromatic aldehydes required as starting materials for the present syntheses are available commercially or their syntheses are reported in the literature. When not otherwise available, the anilines required for the present syntheses are prepared by methods previously set forth by Johnson, U.S. Pat. No. 4,260,764. The latter are converted to the corresponding aromatic bromides and chlorides according to procedures set forth by Bigelow, Organic Syntheses I, pp. 135–137 (1941) and then reacted with magnesium to provide the required Grignard reagents. While a variety of methods are available for the synthesis of the required aldehydes they are also broadly available from the anilines of Johnson. The anilines are converted to the corresponding nitriles by the method of Clarke and Read, Organic Syntheses I, pp. 514–516 (1941). The nitriles are subjected to the Stephen reduction to yield the aldehyde directly. Alternatively, the nitriles are hydrolyzed to acid, then converted to acid chloride and hydrogenated under Rosemund conditions. Acid chlorides can also be converted to the thiol ester and desulfurized to aldehydes according to Wolfram et al., J. Am. Chem. Soc. 68, pp. 1455–1546. Alternatively, aldehydes are obtained from the corresponding benzyl aldehydes by oxidation in dimethylsulfoxide according to Kornblum et al., J. Am. Chem. Soc. 81, pp. 4113–4114. The benzyl bromides are prepared according to methods set forth in Althuis et al., U.S. Pat. No. 4,188,495. Aldehydes are also available by reaction of aromatic Grignard reagents with ethyl orthoformate.

When Z is ($C_5$–$C_{13}$)alkoxy, ($C_8$–$C_{13}$)pyridylalkoxy, or ($C_9$–$C_{14}$)phenylalkoxy (the phenyl group optionally substituted with a chloro or fluoro), the required halide or mesylate, if not available commercially, is readily obtained from the corresponding alcohol using conditions standard in the chemical art. The alcohols in turn are available commercially or by literature methods. For example primary alcohols are available by hydride reduction of aldehydes, acids or esters, while secondary alcohols are available by hydride reduction of ketones. All varieties of alcohols are available by the hydration of olefins, or by the reaction of epoxides with Grignard reagents. Furthermore, many halides suitable for the introduction of the sidechain are available by direct halogenation of olefins or addition of hydrogen halides to olefins.

When the optically active variant of one of the compounds of the present invention is desired, resolution is accomplished by formation and separation of diastereomeric salts derived from an optically active amine/acid with an acidic/basic intermediate or end product according to methods well known in the chemical art. Alternatively, alcohol intermediates are resolved by formation of diasteromeric esters, e.g. optically active amine salts of hemiphthalate esters or are formed directly by use of optically active reagents. It is preferred, however, to carry out the resolution at an early stage in the process in order to avoid unnecessary processing of material which is not desired.

The pharmaceutically acceptable acid addition salts of the present invention are readily prepared by contacting the free base with the appropriate mineral or organic acid in either aqueous solution or in a suitable organic solvent. The salt can then be obtained by precipitation or by evaporation of the solvent. The pharmaceutically acceptable acid addition salts of this invention include, but are not limited to, those formed with hydrochloric, hydrobromic, nitric, phosphoric, sulfuric, benzenesulfonic, citric, laurylsulfonic, fumaric, oxalic, maleic, methanesulfonic, tartaric, p-toluenesulfonic, and succinic acid. With polybasic acids, the salt can include more than one mole of base per mole of acid. However, the acid addition salts which are mole for mole are preferred. If desired, these salts are isolated directly from reaction mixtures by suitable modification of the isolation procedure, without isolation of the intermediate free acid.

The pharmaceutically acceptable cationic salts of the compounds of the present invention are readily prepared by reacting the acid forms with an appropriate base, usually one equivalent, in a co-solvent. By the expression "pharmaceutically acceptable cationic salts"

is intended salts such as the alkali metal salts, e.g., sodium and potassium; alkaline earth metal salts such as calcium and magnesium; aluminum salts; ammonium salts; and salts with organic bases, e.g., amines such as benzathine (N,N'-dibenzylethylenediamine), choline, diethanolamine, ethylenediamine, meglumine (N-methylglucamine), benethamine (N-benzylphenethylamine), diethylamine, piperazine, and tromethamine (2-amino-2-hydroxymethyl-1,3-propanediol). Typical bases employed in the preparation of these cationic salts are sodium hydroxide, sodium methoxide, sodium ethoxide, sodium hydride, potassium methoxide, magnesium hydroxide, calcium hydroxide, benzathine, choline, diethanolamine, ethylenediamine, meglumine, benethamine, diethylamine, piperazine and tromethamine. The salt is isolated by concentration to dryness or by addition of a non-solvent. In some cases, salts can be prepared by mixing a solution of the acid with a solution of a different salt of the cation (e.g., sodium ethylhexanoate, magnesium oleate), employing a solvent in which the desired cationic salt precipitates, or can be otherwise isolated by concentration and/or addition of a non-solvent. If desired, these salts are isolated directly from reaction mixtures by suitable isolation procedures, without isolation of the intermediate free acid.

The analgesic properties of the compounds of this invention are determined by tests using thermal nociceptive stimuli, such as the mouse tail flick procedure, or chemical nociceptive stimuli, such as measuring the ability of a compound to suppress phenylbenzoquinone irritant-induced writhing in mice. These tests and others are described below.

TESTS USING THERMAL NOCICEPTIVE STIMULI

(a)

Mouse Hot Plate Analgesic Testing

The method used is modified after Woolfe and MacDonald, J. Pharmacol. Exp. Ther., 80, 300–307 (1944). A controlled heat stimulus is applied to the feet of mice on a ⅛" thick aluminum plate. A 250 watt reflector infrared heat lamp is placed under the bottom of the aluminum plate. A thermal regulator, connected to thermistors on the plate surface, programs the heat lamp to maintain a constant temperature of 57° C. Each mouse is dropped into a glass cylinder (6½" diameter) resting on the hot plate, and timing is begun when the animal's feet touch the plate. At 0.5 and 2 hours after treatment with the test compound the mouse is observed for the first "flicking" movements of one or both hind feet, or until 10 seconds elapse without such movements. Morphine has an $MPE_{50}=4$–5.6 mg./kg. (s.c.).

(b)

Mouse Tail Flick Analgesic Testing

Tail flick testing in mice is modified after D'Amour and Smith, J. Pharmacol. Exp. Ther., 72, 74–79 (1941), using controlled high intensity heat applied to the tail. Each mouse is placed in a snugfitting metal cylinder, with the tail protruding through one end. This cylinder is arranged so that the tail lies flat over a concealed heat lamp. At the onset of testing, an aluminum flag over the lamp is drawn back, allowing the light beam to pass through the slit and focus onto the end of the tail. A timer is simultaneously activated. The latency of a sudden flick of the tail is ascertained. Untreated mice usually react within 3–4 seconds after exposure to the lamp. The end point for protection is 10 seconds. Each mouse is tested at 0.5 and 2 hours after treatment with morphine and the test compound. Morphine has an $MPE_{50}$ of 3.2–5.6 mg./kg. (s.c.).

(c)

Tail Immersion Procedure

The method is a modification of the receptacle procedure developed by Benbasset, et al., Arch. int. Pharmacodyn., 122, 434 (1959). Male albino mice (19–21 g.) of the Charles River CD-1 strain are weighed and marked for identification. Five animals are normally used in each drug treatment group with each animal serving as its own control. For general screening purposes, new test agents are first administered at a dose of 56 mg./kg. intraperitoneally or subcutaneously, delivered in a volume of 10 ml./kg. Preceding drug treatment and at 0.5 and 2 hours post drug, each animal is placed in the cylinder. Each cylinder is provided with holes to allow for adequate ventilation and is closed by a round nylon plug through which the animal's tail protrudes. The cylinder is held in an upright position and the tail is completely immersed in the constant temperature waterbath (56° C.). The endpoint for each trial is an energetic jerk or twitch of the tail coupled with a motor response. In some cases, the endpoint may be less vigorous post drug. To prevent undue tissue damage, the trial is terminated and the tail removed from the waterbath within 10 seconds. The response latency is recorded in seconds to the nearest 0.5 second. A vehicle control and a standard of known potency are tested concurrently with screening candidates. If the activity of a test agent has not returned to baseline values at the 2-hour testing point, response latencies are determined at 4 and 6 hours. A final measurement is made at 24 hours if activity is still observed at the end of the test day.

TEST USING CHEMICAL NOCICEPTIVE STIMULI

Suppression of Phenylbenzoquinone Irritant-Induced Writhing

Groups of 5 Carworth Farms CF-1 mice are pretreated subcutaneously or orally with saline, morphine, codeine or the test compound. Twenty minutes (if treated subcutaneously) or fifty minutes (if treated orally) later, each group is treated with intraperitoneal injection of phenylbenzoquinone, an irritant known to produce abdominal contractions. The mice are observed for 5 minutes after the injection of the irritant. $MPE_{50}$'s of the drug pretreatments in blocking writhing are ascertained.

TESTS USING PRESSURE NOCICEPTIVE STIMULI

Effect of the Haffner Tail Pinch Procedure

A modification of the procedure of Haffner, Experimentelle Prufung Schmerzstillender, Mittel Deutch Med. Wschr., 55, 731–732 (1929) is used to ascertain the effects of the test compound on aggressive attacking responses elicited by a stimulus pinching the tail. Male albino rats (50–60 g.) of the Charles River (Sprague-Dawley) CD strain are used. Prior to drug treatment, and again at 0.5, 1, 2 and 3 hours after treatment, a Johns Hopkins 2.5-inch "bulldog" clamp is clamped onto the root of the rat's tail. The endpoint at each trial is clear attacking and biting behavior directed toward the offending stimulus, with the latency for attack reported in seconds. The clamp is removed in 30 seconds if attacking has not yet occurred, and the latency of response is recorded as 30 seconds.

TESTS USING ELECTRICAL NOCICEPTIVE STIMULI

The "Flinch-Jump" Test

A modification of the flinch-jump procedure of Tenen, Psychopharmacologia, 12, 278–285 (1968) is used for determining pain thresholds. Male albino rats (175–200 g.) of the Charles River (Sprague-Dawley) CD strain are used. Prior to receiving the drug, the feet of each rat are dipped into a 20% glycerol/saline solution. The animals are then placed in a chamber and presented with a series of 1-second shocks to the feet which are delivered in increasing intensity at 30-second intervals. These intensities are 0.26, 0.39, 0.52, 0.78, 1.05, 1.31, 1.58, 1.86, 2.13, 2.42, 2.72, and 3.04 mA. Each animal's behavior is rated for the presence of (a) flinch, (b) squeak and (c) jump or rapid forward movement at shock onset. Single upward series of shock intensities are presented to each rat just prior to, and at 0.5, 2, 4 and 24 hours subsequent to drug treatment.

Results of the above tests are recorded as percent maximum possible effect (% MPE). The % MPE of each group is statistically compared to the % MPE of the standard and the predrug control values. The % MPE is calculated as follows:

$$\% \ MPE = \frac{\text{test time} - \text{control time}}{\text{cutoff time} - \text{control time}} \times 100$$

The compounds of the present invention are active analgesics via oral and parenteral administration and are conveniently administered in composition form. Such compositions include a pharmaceutical carrier selected on the basis of the chosen route of administration and standard pharmaceutical practice. For example, they are administered in the form of tablets, powders or granules containing such excipients as starch, milk sugar, certain types of clay, etc. Alternatively, they are administered in capsules, in admixtures with the same or equivalent excipients, or in the form of oral suspensions, solutions, emulsions, syrups and elixirs which can contain flavoring and coloring agents. For oral administration of the therapeutic agents of this invention, tablets or capsules containing from about 0.01 to about 100 mg. are suitable for most applications.

The physician will determine the dosage which will be most suitable for an individual patient and it will vary with the age, weight and response of the particular patient and the route of administration. Generally, however, the initial analgesic dosage in adults is from 0.01 to 500 mg. per day in single or divided doses. In many instances, it is not necessary to exceed 100 mg. daily. The favored oral dosage range is from 0.01 to about 300 mg./day; the preferred range is from 0.10 to about 50 mg./day. The favored parenteral dose is from 0.01 to 100 mg./day; the preferred range is from 0.01 to 20 mg./day.

The use of these compounds for the treatment of glaucoma is believed to be due to their ability to reduce intraocular pressure. Their effects on intraocular pressure are determined by tests on dogs. The test drug in instilled into the eye of a dog in the form of a solution or is administered systemically at various periods of time after which the eye is anesthetized by instillation of tetracaine hydrochloride, ½%, 2 drops. A few minutes after this local anesthesia, intraocular pressure readings are taken with a Schiotz mechanical tonometer and after fluorescein dye is administereed, with a Holberg hand application tonometer. The test drug is conveniently used in a solution such as the following: test drug (1 mg.), ethanol (0.05 ml.), Tween 80 (polyoxyalkylene derivative of sorbitan mono-oleate, available from Atlas Powder Co., Wilmington, Del. 19899; 50 mg.) and saline (to make 1 ml.), or in a more concentrated solution wherein the ingredients are present in proportions of 10 mg., 0.10 ml., 100 mg. and 1 ml., respectively. Alternatively the compounds of the present invention are tested for their ability to reduce intraocular pressure in normal rabbits according to the method of Elsohly et al., J. Clin. Pharmacol. 21, pp. 472S–478S (1981). For human use, concentrations of drug from 0.01 mg/kg. to 10 mg./kg. are useful.

Their activity as diuretic agents is determined by the procedure of Lipschitz et al., J. Pharmacol., 79, 97 (1943) which utilizes rats as the test animals. The dosage range for this use is the same as that noted above with respect to their use as analgesic agents.

The antiemetic properties of the compounds of the present invention are determined in unanesthetized unrestrained cats according to the procedure described in Proc. Soc. Exptl. Biol. and Med., 160, 437–440 (1979). The dosage ranges for this utility is also the same as that noted above with respect to their analgesic utility.

This invention also provides pharmaceutical compositions, including unit dosage forms, valuable for the use of the herein described compounds as analgesics and other utilities disclosed herein. The dosage form may be given in single or multiple doses, as previously noted, to achieve the daily dosage effective for a particular utility.

The compounds (drugs) described herein can be formulated for administration in solid or liquid form for oral or parenteral administration. Capsules containing drugs of this invention; i.e.; compounds of formulae (I) to (IV) are prepared by mixing one part by weight of drug with nine parts of excipient such as starch or milk sugar and then loading the mixture into telescoping gelatin capsules such that each capsule contains 100 parts of the mixture. Tablets containing the same compounds are prepared by compounding suitable mixtures of drug and standard ingredients used in preparing tablets, such as starch, binders and lubricants, such that each tablet contains from 0.01 to 100 mg. of drug per tablet.

Suspensions and solutions of these drugs, particularly those wherein A (formulae I and II) is hydroxy, are generally prepared just prior to use in order to avoid problems of stability of the drug (e.g. oxidation) or of suspensions or solution (e.g. precipitation) of the drug upon storage. Compositions suitable for such are generally dry solid compositions which are reconstituted for injectable administration.

The present invention is illustrated by the following examples. However, it should be understood that the invention is not limited to the specific details of these examples.

When compounds containing more than one asymmetric center contain a center of unspecified absolute or relative stereochemistry (e.g. 5-phenyl-2-pentyl) it will be understood by those skilled in the art that the product is a mixture of two diasteroisomers or two racemates, respectively, usually in a ratio of about 1:1.

EXAMPLE 1 trans-1-(3,5-Dimethoxyphenyl)-2-nitroethylene

A solution of 3,5-dimethoxybenzaldehyde (34.5 g., 0.208 mole) and nitromethane (12.69 g., 0.208 mole) in 40 ml. of MeOH was cooled to 0° under $N_2$. A solution was prepared by dissolving NaOH (8.43 g., 0.211 mole) in 10 ml. of $H_2O$ then diluting to 20 ml. with ice-water. This solution was then added dropwise to the methanol mixture. After 15 minutes the reaction was diluted with ice-$H_2O$ and added slowly to a solution of 40 ml. concentrated HCl in 60 ml. $H_2O$. The resulting precipitate (44 g.) was filtered and recrystallized from methanol to give 28.6 g. of product, m.p. 132°; reported, J. Org. Chem. 27, p. 376 (1962), m.p. 133.5°–134.5°.

EXAMPLE 2

4-(2,5-Dimethoxyphenyl)-5-nitrocyclohexene

A steel bomb was charged with product of the preceding Example (28.6 g., 0.134 mole), butadiene (20 g., 0.378 mole), toluene (40 ml.) and a trace of hydroquinone. The bomb was cooled to −78° under $N_2$ atmosphere and sealed rapidly. The sealed tube was heated at 100° for 48 hours. The contents of the bomb were concentrated in a stream of $N_2$ and recrystallized from MeOH to give 29.8 g. of product, m.p. 80.5°–82°; reported, J. Org. Chem. 27, p. 376 (1962), m.p. 73°–75°; $^1$H-NMR (CDCl$_3$) includes 6.40 (3H, s), 5.75 (2H, s), 4.95 (1H, m) and 3.75 (6H, s) ppm.

EXAMPLE 3

6-(3,5-Dimethoxyphenyl)-3-cyclohexen-1-one

The Nef reaction was applied to the product of the preceding Example (28.7 g., 0.109 mole) in 163.5 ml. of ethanol, using 131 ml. of concentrated HCl and the procedure of Wildman, J. Org. Chem. 17, p. 588 (1952) for 6-phenyl-3-cyclohexen-1-ones. After recrystallization from isopropyl ether, there was obtained 23.6 g. of product, m.p. 60°–62°; reported, J. Org. Chem. 27, p. 376 (1962), 65.5°–66.6°.

EXAMPLE 4

2-(3,5-Dimethoxyphenyl)cyclohexanone

Method A

Product of the preceding Example (23.6 g.) in 300 ml. of ethanol was hydrogenated over 3 g. of 10% Pd/C at room temperature and 40 psig to yield, after recrystallization from isopropyl ether, 17 g. of title product, m.p. 61°–62°; reported, J. Org. Chem. 27, p. 376 (1962), 62.5°–63°.

Method B

The method is a modification of that employed by Arnold et al., J. Am. Chem. Soc., 72, 3154 (1950), for preparation of 2-phenylcyclopentanone.

To an ice-cold stirred solution of 3,5-dimethoxyphenyl magnesium bromide, prepared from 25.5 g. of magnesium and 226 g. (1.04 mole) 3,5-dimethoxybromobenzene in 800 ml. dry ethyl ether, is added a solution of 130.5 g. 2-chlorocyclohexanone in 400 ml. dry ethyl ether. The ether is removed by distillation and is replaced with 200 ml. dry xylene. The resulting mixture is heated at 150°–170° C. for two hours, cooled, poured onto ice and diluted with 6N hydrochloric acid. The acidified mixture is extracted with benzene. The organic phase is washed with water and then dilute sodium hydroxide solution, and dried over anhydrous sodium sulfate. The solvents were evaporated in vacuo and the product purified by distillation in vacuo.

EXAMPLE 5

1-(Carbomethoxymethylene)-2-(3,5-dimethoxyphenyl)-cyclohexane

To a suspension of NaH (3.9 g., 0.0814 mole of 50% in oil) in 500 ml. of THF was added dropwise a solution of trimethyl phosphonoacetate (16.2 g., 0.089 mole) in 50 ml. of THF. After stirring 10–15 minutes at room temperature, the ketone product of the preceding Example (17.4 g., 0.074 mole) in 100 ml. of THF was added in one portion. The reaction was heated at 70° for 3 hours, then cooled to 0°. Acetic acid (5.4 g.) was added and the reaction was diluted with $H_2O$ (1 liter) and extracted with ethyl acetate. The extract was dried over $Na_2SO_4$ and evaporated to give 22 g. of crude product. Recrystallization from isopropyl ether gave 20.4 g. of product, m.p. 80°–81°; $^1$H-NMR (CDCl$_3$) includes 6.34 (3H, s), 5.20 (1H, s), 3.80 (6H, s) and 3.60 (3H, s) ppm.

EXAMPLE 6

1-(Carboxymethylene)-2-(3,5-dimethoxyphenyl)cyclohexane and

2-[2-(3,5-Dimethoxyphenyl)cyclohexane-1-yl]acetic Acid

Method A

To a solution of the ester product of the preceding Example (20 g.) in a mixture of 100 ml. MeOH, 50 ml. $H_2O$ and 50 ml. THF was added 42 ml. of 5N NaOH. The reaction was heated on a steam bath for 3 hours then diluted with ice-water. A solution of 1N HCl (220 ml.) was added and the reaction mixture was extracted with ethyl acetate, dried over $Na_2SO_4$ and evaporated to give 20 g. of crude product. Recrystallization from $CH_2Cl_2$/ether gave 16.7 g. of the carboxymethylene product, m.p. 154°–156°; $^1$H-NMR (CDCl$_3$) 6.30 (3H, s), 3.70 (6H, s), 5.15 (1H, s), 10.90 (1H, s) ppm.

Method B

Product prepared according to the preceding Example (68.8 g., 0.230 mole) was combined with 350 ml. of methanol and 142.4 ml. (0.711 mole) of 5N NaOH and the mixture heated to reflux for 1.3 hours. The reaction mixture was cooled to room temperature, quenched with 62.2 ml. of concentrated HCl and water and extracted 3× with ethyl acetate. The combined organic extracts were washed with brine, dried over $MgSO_4$, filtered and stripped of solvents. The residue was recrystallized from $CH_2Cl_2$/ether to yield the carboxymethylene product in two crops: 37.6 g., m.p. 155°–158°; 13.3 g., m.p. 156°–158°. The mother liquor from the second crop was evaporated to solids (13.5 g.) which on trituration with isopropyl ether gave a further 4 g. of the carboxymethylene product, m.p. 152°–156° C., ir (KBr) 1675 cm$^{-1}$. The isopropyl ether triturate was evaporated to yield the non-conjugated substituted acetic acid product [9 g., ir (KBr) 1705 cm$^{-1}$].

EXAMPLE 7

2S*-[2R*-(3,5-Dimethoxyphenyl)cyclohexyl]acetic Acid

Lithium metal (832 mg., 0.119 mole) was added to a solution of the alpha,beta-unsaturated acid of the preceding Example (15 g., 0.054 mole) in 1 liter liquid $NH_3$ and 200 ml. THF at $-33°$. A blue color was allowed to form and persist for 2 minutes. The reaction was then quenched by addition of 15 g. of $NH_4Cl$. The $NH_3$ was evaporated under a stream of $N_2$. Water (200 ml.) was added and the solution was acidified to pH 3.5 by addition of 6N HCl. The aqueous layer was then extracted with $CH_2Cl_2$ and the organic layer was dried over $Na_2SO_4$ and evaporated to give 15 g. of crude product which was triturated with hexane and filtered to give 14 g. of product, m.p. 110°–111.5°; $^1$H-NMR ($CDCl_3$) includes 2.16 (2H, dd, J=14.7, 2.3), 2.17 (1H, td, J=11, 3), 1.90 (1H, d, J=14.6) ppm.

EXAMPLE 8

2,3,4,4aR*,10,10aS*-Hexahydro-6,8-dimethoxy-1H-phenanthren-9-one

Trifluoroacetic anhydride (20 ml.) was added dropwise to a solution of the acid of the preceding Example (14.7 g.) in trifluoroacetic acid (28 ml.) at 0°. After stirring for 15 minutes, the volatiles were evaporated and the residue was taken up in $CH_2Cl_2$ and washed with $H_2O$, 20% $NaHCO_3$ and brine, then dried over $Na_2SO_4$ and evaporated to give 15.7 g. of crude product which was recrystallized from ether to give 12.5 g. of product, m.p. 110°–111°; MS exact mass calcd. for $C_{16}H_{20}O_3$: 260.3358; found: 260.1404.

EXAMPLE 9

2,3,4,4aR*,10,10aS*-Hexahydro-6,8-dihydroxy-1H-phenanthren-9-one

A solution of the ketone of the preceding Example (12.3 g.) in a mixture of 220 ml. acetic acid and 220 ml. of 48% HBr was heated at 100° in a $N_2$ atmosphere for 36 hours. The volatiles were evaporated under reduced pressure and the residue was purified by chromatography on 120 g. of silica gel eluting with ethyl acetate to give 12 g. of material, m.p. 189°–200°. Recrystallization from ethyl acetate/$CHCl_3$ gave 10 g. of product, m.p. 200°–201°; $^1$H-NMR (acetone-$d_6$) includes 6.50–6.10 (2H, m) and 13.0 (1H, s); M.S. exact mass calcd. for $C_{14}H_{16}O_3$: 232.2816; found: 232.1097.

EXAMPLE 10

2,3,4,4aR*,10,10aS*-Hexahydro-8-hydroxy-6-(5-phenyl-2-pentyloxy)-1H-phenanthren-9-one A mixture of the phenol of the preceding Example (9.9 g., 0.043 mole) and $K_2CO_3$ (7.1 g., 0.103 mole) in 120 ml. DMF was heated at 70° for 30 minutes. 5-Phenyl-2-pentyl mesylate (13.55 g., 0.056 mole) in 10 ml. of DMF was added in one portion and the mixture was heated in a nitrogen atmosphere at 80° overnight. The reaction was diluted with ice-$H_2O$ and extracted with ethyl acetate. The extract was dried over $Na_2SO_4$ and evaporated to give 21 g. of crude product. Chromatography on 750 g. of silica gel with $CHCl_3$/hexane (50/50), then with $CHCl_3$, and finally 20% ether in $CHCl_3$ gave 14 g. of product as an oil; $^1$H-NMR ($CDCl_3$) includes 13.10 (1H, s), 7.30 (5H, s), 6.50–6.20 (2H, m), 4.45 (1H, m), 1.40 (3H, d) ppm. As a result of the asymmetric carbon introduced in the 5-phenyl-2-pentyloxy side chain, this product is a mixture of two racemic compounds, i.e. two racemates or two racemic pairs.

By the same procedure, the appropriate mesylate esters are reacted with the phenol of the preceding Example to yield
2,3,4,4aR*,10,10aS*-hexahydro-8-hydroxy-6-(4-phenyl-1-butoxy)-1H-phenanthren-9-one;
2,3,4,4aR*,10,10aS*-hexahydro-8-hydroxy-6-[3-(3-pyridyl)-1-propoxy]-1H-phenanthren-9-one;
2,3,4,4aR*,10,10aS*-hexahydro-8-hydroxy-6-(2-decyloxy)-1H-phenanthren-9-one (two racemates); and
2,3,4,4aS,10,10aR-hexahydro-8-hydroxy-6-(5-phenyl-2R-pentyloxy)-1H-phenanthren-9-one and
2,3,4,4aR,10,10aS-hexahydro-8-hydroxy-6-(5-phenyl-2R-pentyloxy)-1H-phenanthren-6-one.

EXAMPLE 11

10-Formyl-2,3,4,4aR*,10,10aR*-hexahydro-8-hydroxy-6-(5-phenyl-2-pentyloxy)-1H-phenanthren-9-one In a 1 liter flask fitted with magnetic stirrer, condenser and $N_2$ inlet was placed 50% NaH in mineral oil (5.52 g., 0.115 mole) and washed with two portions of hexane to remove the mineral oil. In sequence, ether (800 ml.), title product of the preceding Example (12.5 g., 0.033 mole), and, dropwise, ethyl formate (41.2 ml.), followed by 4 drops of ethanol. The reaction mixture was refluxed with 3 hours, cooled to room temperature, stirred for 64 hours at room temperature then poured over crushed ice, acidified with 115 ml. 1N HCl, and extracted with 3 portions of ethyl acetate. The combined organic extracts were washed with brine, dried over $MgSO_4$, filtered and stripped of solvents. The residue was chromatographed on 200 g. silica gel eluting with $CHCl_3$ and monitoring by tlc [$R_f$ 0.9 (20:1 $CHCl_3$:isopropyl ether)]. On evaporation, product fractions gave 10.1 g. of title product as an oil, $^1$H-NMR ($CDCl_3$) includes 7.20 (5H, s), 6.20 (2H, m), 12.30 (1H, s), 13.60 (1H, d) ppm. The product is a mixture of two racemates. No additional asymmetry is introduced by introduction of the 5-formyl group because of the tendency of this group to exist, together with the 6-ketone, in an enolic form.

By the same method, other ketones of the preceding Examples are converted to:
10-formyl-2,3,4,4aR*,10,10aR*-hexahydro-8-hydroxy-6-(4-phenyl-1-butoxy)-1H-phenanthren-9-one;
10-formyl-2,3,4,4aR*,10,10aR*-hexahydro-8-hydroxy-6-[3-(3-pyridyl)-1-propoxy]-1H-phenanthren-9-one;
10-formyl-2,3,4,4aR*,10,10aR*-hexahydro-8-hydroxy-6-(2-decyloxy)-1H-phenanthren-9-one (two racemates);
10-formyl-2,3,4aR,10,10aR-hexahydro-8-hydroxy-6-(5-phenyl-2R-pentyloxy)-1H-phenanthren-9-one; and
10-formyl-2,3,4aS,10,10aS-hexahydro-8-hydroxy-6-(5-phenyl-2R-pentyloxy)-1H-phenanthren-9-one.

EXAMPLE 12

2,3,4,4aR*,10S*,10aR*-Hexahydro-8-hydroxy-10-(3-oxo-1-butyl)-6-(5-phenyl-2-pentyloxy)-1H-phenanthren-9-one Title product of the preceding Example (10.0 g., 24.6 mmoles) was combined with 40 ml. methanol, 18 ml. THF, methyl vinyl ketone (3.4 g., 49.2 mmoles) and triethylamine (0.829 g., 8.2 mmoles) and stirred under nitrogen for 16 hours, at which time an additional 0.329 g. (3.25 mmoles) of triethylamine and 1.34 g. of methyl vinyl ketone (19 mmoles) were added. After stirring for an additional 24 hours, the reaction mixture was stripped of solvents in vacuo, and the residue taken up in ethyl acetate, washed 2× with 10% Na$_2$CO$_3$, 1× with H$_2$O and 1× with brine, dried over MgSO$_4$, filtered and evaporated to crude product. To ensure complete deformylation, the crude product was taken into 150 ml. methanol/30 ml. THF at 0°. K$_2$CO$_3$ (0.859 g.) was added and the mixture stirred for 2 hours, filtered and stripped of solvent. Chromatography of the residual oil on 200 g. of silica gel, eluting with 4:1 CHCl$_3$:ether and monitoring by tlc gave purified title product, as a mixture of at least two racemates. The relative stereochemistry at C-5 has not been established—while both diastereomeric pairs may be present, it is most likely that relative stereochemistry at C-5 is S*, and is thus unchanged in the process of the next Example. The yield of title product was 8.4 g. [oil; R$_f$ 0.45 (6:1 hexane:ether), 0.1 elongated (CHCl$_3$); $^1$H-NMR (CDCl$_3$) includes 13.20 (1H, s), 7.20 (5H, s), 6.30 (2H, m), 2.10 (3H, s), 1.30 (3H, d) ppm].

By the same method, the other 5-formyl derivatives of the preceding Example are converted to:

2,3,4aR*,10S*,10aR*-hexahydro-8-hydroxy-10-(3-oxo-1-butyl)-6-(4-phenyl-1-butoxy)-1H-phenanthren-9-one;

2,3,4aR*,10S*,10aR*-hexahydro-8-hydroxy-10-(3-oxo-1-butyl)-6-[3-(3-pyridyl)-1-propoxy]-1H-phenanthren-9-one;

2,3,4aR*,10S*,10aR*-hexahydro-8-hydroxy-10-(3-oxo-1-butyl)-6-(2-decyloxy)-1H-phenanthren-9-one;

2,3,4aR,10S,10aR-hexahydro-8-hydroxy-10-(3-oxo-1-butyl)-6-(5-phenyl-2R-pentyloxy)-1H-phenanthren-9-one; and 2,3,4aS,10R,10aS-hexahydro-8-hydroxy-10-(3-oxo-1-butyl)-6-(5-phenyl-2R-pentyloxy)-1H-phenanthren-9-one.

EXAMPLE 13

2,3,4,4aS*,4bS*,5,6,12bR*-Octahydro-9-hydroxy 11-(5-phenyl-2-pentyloxy)-1H-triphenylen-7-one Under nitrogen, KOH (42.5 g., 0.759 mole) was dissolved with stirring in 380 ml. of methanol. Title product of the preceding Example (8.4 g., 18.8 mmoles) was added and the stirred reaction mixture heated at 50° C. for 1 hour, cooled and stirred at room temperature for 16 hours, cooled to 0° C. and neutralized by the addition of 45.6 g. (0.76 mole) of glacial acetic acid. Volatile materials were removed by evaporation and the residue dissolved in ethyl acetate, washed 2× water and 1× brine, dried over MgSO$_4$, filtered and stripped of solvent. The latter residue was chromatographed on 200 g. of silica gel, eluting first with CHCl$_3$ and then with 4:1 CHCl$_3$:ether and monitoring by tlc. Clean fractions were combined and evaporated to yield 7.0 g of title product, a mixture of two racemates, m.p. 160°–165°; R$_f$ 0.3 (2:1 CHCl$_3$:ether); ir (CHCl$_3$) 1585, 1560 cm$^{-1}$. A sample triturated with ether gave m.p. 189°–190°.

By the same method, the other ketones of the preceding Example are cyclized, affording:

2,3,4,4aS*,4bS*,5,6,12bR*-octahydro-9-hydroxy-11-(4-phenyl-1-butoxy)-1H-triphenylen-7-one;

2,3,4,4aS*,4bS*,5,6,12bR*-octahydro-9-hydroxy-11-[3-(3-pyridyl)-1-propoxy]-1H-triphenylen-7-one;

2,3,4,4aS*,4bS*,5,6,12bR*-octahydro-9-hydroxy-11-(2-decyloxy)-1H-triphenylen-7-one;

2,3,4,4aS,4bS,5,6,12bR-octahydro-9-hydroxy-11-(5-phenyl-2R-pentyloxy)-1H-triphenylen-7-one; and 2,3,4,4aR,4bR,5,6,12bS-octahydro-9-hydroxy-11-(5-phenyl-2R-pentyloxy)-1H-triphenylen-7-one.

EXAMPLE 14

9-Acetoxy-2,3,4,4aS*,4aS*,4bS*,5,6,8,8aR*,12bR*-decahydro-11-(5-phenyl-2-pentyloxy)-1H-triphenylen-7-one and 9-Acetoxy-2,3,4,4aS*,4bS*,5,6,8,8aS*,12bR*-decahydro-11-(5-phenyl-2-pentyloxy)-1H-triphenlene-7-one The title ketone of the preceding Example (2.66 g., 6.2 mmoles) was slurried in a mixture of 150 ml. of THF and 300 ml. of liquid NH$_3$ at −33°. Sufficient Li metal (in excess of 98 mg., 14 mmoles) was added in portions until the blue color persisted for 4 minutes. The reaction was then quenched by the addition of 2.6 g. of NH$_4$Cl (48 mmole) and the ammonia removed by evaporation under a stream of nitrogen. Water and ethyl acetate were added, the pH was adjusted to 6, and the aqueous layer separated and extracted with additional ethyl acetate. The organic layers were combined, washed with brine, dried over MgSO$_4$, filtered and stripped of solvent to yield a mixture of intermediate trans (4bS*,8aR*) and cis (4bS*,8aS*) phenolic ketones (2.7 g.). The mixed produced was taken up in 50 ml. CH$_2$Cl$_2$. Triethylamine (5 g.) and acetic anhydride (2.5 g.) were added and the solution allowed to stand at room temperature under nitrogen for 16 hours. Solvent was removed by evaporation and the residue was taken into ether, washed with water and then brine, dried over MgSO$_4$, filtered and stripped of solvent to yield 3.3 g. of a mixture of title products. The mixture was chromatograhed on 150 g. silica gel, gradiently eluted with 1:9, 1:4 and 1:1 ether:hexane. There was isolated 0.6 g. of the less polar, trans (4bS*,8aR*) fused product [oil, $^1$H-NMR (CDCl$_3$) includes 7.20 (5H, s), 6.65 (1H, d), 6.40 (1H, d), 3.35 (2H, m), 2.30 (3H, s) ppm]. Additional mixed product from the column was rechromatographed on 400 g. of fresh silica gel, gradiently eluting with 1:20, 1:10, 1:5 and 2:3 ether:hexane, yielding an additional 0.7 g. of the less polar product, and 0.3 g. of the more polar cis (4bS*,8aS*) fused product [oil; $^1$H-NMR (CDCl$_3$) includes 7.20 (5H, s), 6.65 (1H, d), 6.40 (1H, d), 2.30 (3H, s)]. Each of these products is a pair of racemates.

By the same method the following compounds are prepared from other ketones of the preceding Example:

9-acetoxy-2,3,4,4aS*,4bS*,5,6,8,8aR*,12bR*-decahydro-11-(4-phenyl-1-butoxy)-1H-triphenylene-7-one (4b,8a-trans) and the corresponding 4b,8a-cis compound;

9-acetoxy-2,3,4,4aS*,4bS*,5,6,8,8aR*,12bR*-decahydro-11-[3-(3-pyridyl)-1-propoxy]-1H-triphenylen-7-one (4b,8a-trans) and the corresponding 4b,8a-cis compounds;

9-acetoxy-2,3,4,4aS*,4bS*,5,6,8,8aR*,12bR*-decahydro-11-(2-decyloxy)-1H-triphenylen-7-one (4b,8a-trans, two racemates) and the corresponding 4b,8a-cis compounds;

9-acetoxy-2,3,4,4aS,4bs,5,6,8,8aR,12bR-decahydro-11-(5-phenyl-2R-pentyloxy)-1H-triphenylene-7-one (4b,8a-trans) and the corresponding 4b,8a-cis isomer; and 9-acetoxy-2,3,4aR,4bR,5,6,8,8aR,12bS-decahydro-11-(5-phenyl-2R-pentyloxy)-1H-triphenylen-7-one (4b,8a-cis) and the corresponding 4b,8a-trans isomer.

Substituting an equivalent amount of benzoic anhydride, succinic anhydride or 5-(4-methylpiperazino)valeroyl chloride hydrochloride for the acetic anhydride in this Example affords the corresponding 9-benzoate, 9-(3-carboxypropionate) and 9-[5-(4-methylpiperazino)-valerate]esters.

EXAMPLE 15

2S*-[2S*-(2,5-Dimethoxyphenyl)-1-cyclohexyl]acetic Acid

2-[2-(3,5-Dimethoxyphenyl)cyclohexen-1-yl]acetic acid (3 g.) from Example 6 was hydrogenated with 1.5 g 5% palladium-on-carbon catalyst and 100 ml. ethanol in a pressure bottle at 50 psi (3.5 kg/cm$^2$) until substantially 1 equivalent of hydrogen is taken up. The catalyst was recovered by filtration and the filtrate saturated with dry hydrogen chloride, converting the title product to the ethyl ester, isolated by stripping the solvent. The crude ester was chromatographed on 300 g. of silica gel with 9:1 hexane:ether as eluant. Less polar impurities (20 mg.) were discarded and 2 g. of purified ethyl ester recovered from intermediate fractions. The ester was hydrolyzed with 4 ml. of 5N NaOH and 10 ml. of methanol gently refluxed for 1.5 hours. The reaction mixture was cooled, acidified with dilute HCl and extracted with ethyl acetate. The organic extract was washed with brined, dried (MgSO$_4$), filtered and stripped of solvent. Recrystallization of the residue from isopropyl ether gave purified title product (1.1 g., m.p. 139°–141° C.).

EXAMPLE 16

2,3,4aS*,10,10aS*-Hexahydro-6,8-dimethoxy-1H-phenanthren-9-one

By the method of Example 8, the acid of the preceding Example is cyclized to title product.

EXAMPLE 17

2,3,4aS*,10,10aS*-Hexahydro-6,8-dihydroxy-1H-phenanthren-9-one

By the method of Example 9, the dimethyl ether of the preceding Example is hydrolyzed to the title product.

EXAMPLE 18

2,3,4aS*,10,10aS*-Hexahydro-8-hydroxy-6-(5-phenyl-2-pentyloxy)-1H-phenanthren-9one By the method of Example 10, the bis-phenol of the preceding Example is alkylated to title product.

By the same method the bis-phenol of the preceding Example is reacted with 5-phenyl-2S-pentyl mesylate to produce 2,3,4aS,10,10aS-hexahydro-8-hydroxy-6-(5-phenyl-2R-pentyloxy)-1H-phenanthren-9-one and 2,3,4,aR,10,10aR-hexahydro-8-hydroxy-6-(5-phenyl-2R-pentyloxy)-1H-phenanthren-9-one.

EXAMPLE 19

10-Formyl-2,3,4aS*,10,10aR*-hexahydro-8-hydroxy-6-(5-phenyl-2-pentyloxy)-1H-phenanthren-9-one By the method of Example 11, the title product of the preceding Example is formylated to yield the title 10-formyl derivative.

By the same method the other compounds of the preceding Example are converted to:
10-formyl-2,3,4aR,10,10aS-hexahydro-8-hydroxy-6-(5-phenyl-2R-pentyloxy)-1H-phenanthren-9-one; and
10-formyl-2,3,4aS,10,10aR-hexahydro-8-hydroxy-6-(5-phenyl-2R-pentyloxy)-1H-phenanthren-9-one.

EXAMPLE 20

2,3,4,4aS*,10S*,10aR*-Hexahydro-8-hydroxy-10-(3-oxo-1-butyl)-6-(5-phenyl-2-pentyloxy)-1H-phenanthren-9-one and 2,3,4,4aS*,10R*,10aR*-Hexahydro-8-hydroxy-10-(3-oxo-1-butyl)-6-(5-phenyl-2-pentyloxy)-1H-phenanthren-9-one By the procedure of Example 12, title product of the preceding Example is reacted with methyl vinyl ketone and deformylated to produce a mixture of title products.

By the same method, the other products of the preceding Example are converted to:
2,3,4aR,10S,10aS-hexahydro-8-hydroxy-10-(3-oxo-1-butyl)-6-(5-phenyl-2R-pentyloxy)-1H-phenanthren-9-one and 2,3,4aR,10R,10aS-hexahydro-8-hydroxy-10-(3-oxo-1-butyl)-6-(5-phenyl-2R-pentyloxy)-1H-phenanthren-9-one; and
2,3,4aS,10R,10aR-hexahydro-8-hydroxy-10-(3-oxo-1-butyl)-6-(5-phenyl-2R-pentyloxy)-1H-phenanthren-9-one and 2,3,4aS,10S,10aR-hexahydro-8-hydroxy-10-(3-oxo-1-butyl)-6-(5-phenyl-2R-pentyloxy)-1H-phenanthren-9-one.

EXAMPLE 21

By the procedure of Example 13, the products of the preceding Example are cyclized, producing:
2,3,4aS*,4bS*,5,6,12bS*-octahydro-9-hydroxy-11-(5-phenyl-2-pentyloxy)-1H-triphenylen-7-one (4a,4b-trans);
2,3,4aS*,4bR*,5,6,12bS*-octahydro-9-hydroxy-11-(5-phenyl-2-pentyloxy)-1H-triphenylen-7-one (4a,4b-cis);
2,3,4aS,4bS,5,6,12bS-octahydro-9-hydroxy-11-(5-phenyl-2R-pentyloxy)-1H-triphenylen-7-one;
2,3,4aS,4bR,5,6,12bS-octahydro-9-hydroxy-11-(5-phenyl-2R-pentyloxy)-1H-triphenylen-7-one;
2,3,4aR,4bR,5,6,12bR-octahydro-9-hydroxy-11-(5-phenyl-2R-pentyloxy)-1H-triphenylen-7-one; and
2,3,4aR,4bS,5,6,12bR-octahydro-9-hydroxy-11-(5-phenyl-2R-pentyloxy)-1H-triphenylen-7-one.

EXAMPLE 22

By the procedure of Example 14, the following compounds are obtained by Li/NH$_3$ reduction of the compounds of the preceding Example to preferentially yield 4b,8a-trans-fused compounds as follows:
2,3,4,4aS*,4bS*,5,6,8,8aR*,12bS*-decahydro-9-hydroxy-11-(5-phenyl-2-pentyloxy)-1H-triphenylene-7-one (4a,4b-trans, 4b,8a-trans);

2,3,4,4aS*,4bR*,5,6,8,8aS*,12bS*-decahydro-9-hydroxy-11-(5-phenyl-2-pentyloxy)-1H-triphenylen-7-one (4a,4b-cis, 4b,8a-trans);

2,3,4,4aS,4bS,5,6,8,8aR,12bS-decahydro-9-hydroxy-11-(5-phenyl-2R-pentyloxy)-1H-triphenylen-7-one;

2,3,4,4aS,4bR,5,6,8,8aS,12bS-decahydro-9-hydroxy-11-(5-phenyl-2R-pentyloxy)-1H-triphenylen-7-one;

2,3,4,4aR,4bR,5,6,8,8aS,12bR-decahydro-9-hydroxy-11-(5-phenyl-2R-pentyloxy)-1H-triphenylen-7-one; and 2,3,4,4aR,4bS,5,6,8,8aR,12bR-decahydro-9-hydroxy-11-(5-phenyl-2R-pentyloxy)-1H-triphenylen-7-one.

EXAMPLE 23

By the procedure of Example 21, the compounds of the preceding Example are acetylated to yield the corresponding 9-acetoxy derivatives.

PREPARATION 1

5-Phenyl-2-pentyl Mesylate

To a stirred solution of 5-phenyl-2-pentanol (482 g.; 2.94 moles) in tetrahydrofuran (2250 ml.) at 0° C. was added methanesulfonyl chloride (300 ml.) at such a rate that the internal temperature does not rise above 10° C. (total addition time 4.5 hours). After addition is complete, the reaction mixture was allowed to warm to room temperature and stirring was continued for an additional hour. The reaction mixture was filtered and the supernate concentrated to a light yellow oil (2800 g.) which was dissolved in chloroform (2 liters) and washed with water (4×1 liter), brine (1×1 liter), charcoal treated (50 g.), dried (MgSO$_4$), filtered through diatomaceous earth and concentrated to a light orange oil (687 g., 95% yield). This material was suitable for use without further purification.

$^1$H-NMR (CDCl$_3$): 7.23 (s, 5H, aromatic), 4.53–5.13 (m, 1H, —CH—O—), 2.93 (s, 3H, O—SO$_2$—CH$_3$), 2.42–2.93 (m, 2H, —C$\underline{H}_2$C$_6$H$_5$), 1.50–1.92 [m, 4H, —(CH$_2$)$_2$—], 1.23 (s, 3H, O—CH—C$\underline{H}_3$) ppm.

PREPARATION 2

5-Phenyl-2R-pentyl Mesylate

By the method of Preparation 1, 5-phenyl-2R-pentanol is converted to title product.

PREPARATION 3

5-Phenyl-2S-pentyl Mesylate

By the method of Preparation 1, 5-phenyl-2S-pentanol was converted to title product.

Likewise, 4-phenyl-2S-butanol and 6-phenyl-2S-hexanol are converted to the corresponding mesylates.

PREPARATION 4

4-Phenyl-1-butyl Mesylate

By the method of Preparation 1, 4-phenyl-1-butanol was converted to title product, a yellow oil; m/e 228; $^1$H-NMR (CDCl$_3$): 7.22 (bs, 5H, aromatic), 4.08–4.34 (m, 2H, —CH$_2$—O—), 3.93 (s, 3H, SO$_2$CH$_3$), 2.40–2.82 (m, 2H, C$\underline{H}_2$C$_6$H$_5$), 1.51–1.93 (m, 4H, —CH$_2$CH$_2$—) ppm.

PREPARATION 5 d(+)-2-Octyl mesylate
and
1(−)-2-Octyl mesylate

By the method of Preparation 1, the optically active forms of 2-octanol were converted to:

1(−)-2-octyl mesylate, a colorless oil, [alpha]$_D^{25}$ = −9.695° (CHCl$_3$, C=2.6), $^1$H-NMR (CDCl$_3$): 4.79 (bg, 1H, —CH—O—), 2.97 (s, 3H, S—CH$_3$), 1.40 (d, 3H, C$\underline{H}_3$—CH), 0.87 (t, 3H, C$\underline{H}_3$CH$_2$), 1.0–2.0 [m, 10H, —(CH$_2$)$_5$—] ppm; and d(+)-2-octyl mesylate, [alpha]$_D^{25}$ = +9.238° (CHCl$_3$, C=2.8), $^1$H-NMR identical to the 1(−) form.

PREPARATION 6

By the method of Preparation 1, the following mesylates are prepared from the corresponding alcohols:
2-phenyl-1-butyl mesylate;
3-phenyl-1-butyl mesylate;
1-phenyl-2-butyl mesylate;
4-phenyl-2-butyl mesylate;
5-phenyl-1-pentyl mesylate;
3-(3-pyridyl)-1-propyl mesylate;
1-tridecanyl mesylate;
1-dodecyl mesylate;
2-decyl mesylate;
4-decyl mesylate;
3-octyl mesylate;
4-heptyl mesylate;
5-methyl-2-hexyl mesylate;
4-methyl-1-pentyl mesylate;
1-(3-chlorophenyl)-1-butyl mesylate; and
1-(3-fluorophenyl)-1-propyl mesylate.

PREPARATION 7

Ethyl 2-(2-Phenylethyl)acetoacetate

Ethyl acetoacetate (53.8 g., 0.29 mole) was dissolved in 110 ml. of anhydrous ethanol. Sodium methoxide (17.3 g., 0.36 mole) was added portionwise to the stirred solution, allowing the temperature to rise to 40°–50°. The mixture was then heated to reflux (80°–82°) and phenethyl bromide (53.8 g., 0.32 mole) added dropwise over 1 hour. Reflux was continued for 20 hours. The reaction mixture was cooled to 30°–35° and filtered over diatomaceous earth with ethanol wash. The combined filtrate and wash were concentrated in vacuo to a pot temperature of 50°, cooled to 25°, diluted with 150 ml. of hexane and 40 ml. of water, acidified to pH 6.5–7.0 with 6N HCl. The hexane layer was separated and washed with 25 ml. of fresh water. The aqueous layers were combined and back-washed with 40 ml. of fresh hexane. The hexane layers were combined, washed with 60 ml. of water, dried over 15 g. MgSO$_4$, filtered and evaporated to yield title product as an oil (62 g., 91%).

PREPARATION 8

5-Phenyl-2-pentanone

Product of the preceding Preparation (30.5 g., 0.13 mole) was combined with 130 ml. of ethanol, 25 ml. of water and KOH (85%, 20.6 g, 0.31 mole). The reaction mixture was refluxed for 3 hours, cooled, concentrated in vacuo to 80 ml., and diluted with 90 ml. of water and 60 ml. of hexane. The water layer was separated and washed with 40 ml. of fresh hexane. The combined organic layers were back-washed with 30 ml. of water, dried (MgSO₄), filtered and stripped of solvent to yield 12.8 g. of crude product as an oil, purified by distillation (9.5 g., b.p. 104°/2 mm.).

PREPARATION 9

5-Phenyl-2-pentanol

Under nitrogen, sodium borohydride (755 mg., 0.02 mole) was dissolved in 30 ml. of absolute ethanol and cooled to 0°–5°. Ketone of the preceding Preparation (10.3 g., 0.064 mole) was added dropwise with stirring over 30 minutes, maintaining the temperature 5°–15°. The temperature was increased to 22° for 2 hours, and then reduced to 10°–12° as 3 ml. of methanol was added over 5 minutes and 2 ml. of concentrated HCl was added over 30 minutes. The quenched reaction mixture was poured into 20 ml. of water and extracted with hexane (50 ml.). The extract was dried (MgSO₄), filtered, concentrated to an oil and distilled to yield title product (8.7 g., 83%, b.p. 90°–100°/0.3 mm.).

PREPARATION 10

5-Phenyl-2-pentyl Hydrogen Phthalate

Phthalic anhydride (21.5 g., 0.145 mole) was stirred with the alcohol of the preceding Preparation (23.7 g., 0.145 mole) and heated to 90°. The temperature is gradually increased to 130°, an exotherm occuring at some point above 90°. The temperature, when the exotherm occurs is not allowed to rise above 155°. Following the exotherm, the reaction is maintained at 130°–140° for 1 hour, then cooled to 50° and diluted with 125 ml. of acetonitrile. The resulting solution of title product is used directly in the next step.

PREPARATION 11

5-Phenyl-2S-pentyl Brucine Phthalate

Brucine (57.6 g., 0.146 mole) in 105 ml. of acetonitrile was added to the acetonitrile solution of ester from the preceding Preparation and the mixture heated to 55°–60°. Maintaining this temperature, isopropyl ether (610 ml.) is added in a steady stream. The solution is cooled gradually to 23°, and the crystalline material which begins to form at 45°–55°, granulated for 16 hours, recovered by filtration and air dried at 55° (33 g.). Highly resolved material has $[alpha]_D^{CHCl_3} +40.0$. If at this stage the rotation is less than +38.5°, it is recrystallized from acetonitrile-isopropyl ether (for 33 g. of crude, 130 ml. of acetonitrile and 300 ml. of isopropyl ether was used, with recovery of 26 g. of purified title product).

PREPARATION 12

5-Phenyl-2S-pentanol

S-Brucine salt of the preceding Preparation (10.0 g., 14.2 mmoles) was combined with 125 ml. of toluene and 150 ml. of water. With stirring the pH was adjusted to 1.7 with about 6 ml. of 3N HCl. The aqueous layer was separated and extracted 2×40 ml. toluene. Brucine was precipitated from the aqueous layer by adjusting the pH to 11.5 with 50% NaOH. Recrystallization from isopropyl alcohol provides material suitable for reuse. The toluene layers were combined, back-washed with 75 ml. of water, concentrated to 45–50 ml. Fresh water (65 ml.) and then KOH (85%, 1.90 g., 28.8 mmoles) were added and the mixture stirred for 1 hour at room temperature and then 2 hours at 82°–84°. The reaction mixture was cooled to 25°, the toluene layer separated and the aqueous layer washed 3×20 ml. toluene. The toluene layers were combined, washed 1×20 ml. saturated NaCl, dried (MgSO₄), filtered and concentrated to yield title product as an oil (1.91 g.), purified by distillation in vacuo (1.64 g., b.p. 85°–92°/0.1 mm., $[alpha]_D^{25} +8.24°$ to +8.57°).

PREPARATION 13

5-Phenyl-2R-pentanol

To a solution of racemic 5-phenylpentan-2-ol (4.9 g., 0.03 mole) in 50 ml. toluene was added d-mandelic acid (4.5 g., 0.03 mole) and a trace of p-toluenesulfonic acid. This mixture was heated for 10 hours at reflux using a Dean Stark device to remove water. Upon cooling, 50 ml. of benzene was added and the reaction washed with 3×100 ml. of saturated NaHCO₃ solution, the organic phase dried (MgSO₄) and concentrated to yield 7.0 g. of a colorless oil (78%). A portion of this oil (5.4 g.) was subjected to column chromatographic separation using 500 g. of silica gel and an ethyl ether-hexane (1 to 4) solvent system. The separation of the diastereomeric mandelates could conveniently be followed by ¹H-NMR. The first eluting 5-phenyl-2R-pentanol had the CH₃ doublet (J=7.0) centered at 1.05 ppm and the second eluting 5-phenyl-2S-pentanol at 1.25 ppm. Using a fraction collector, 150 15 ml. fractions were collected from the above column. Fractions 101–110 show an isomer ratio of ca. 95:5 of the first eluting isomer (HPLC). These fractions were combined and concentrated to yield 0.90 g.; $[alpha]_D^{25} = 37.56°$ (CHCl₃).

A portion of the purified first eluting isomer (0.80 g., 0.0027 mole) was dissolved in 25 ml. of methanol and 2.0 ml. of H₂O and 0.50 g. of K₂CO₃ (0.0036 mole) was added and this reaction stirred for 24 hours at 25°. Water (10 ml.) was then added and the reaction extracted with 2×25 ml. of EtOAc; the organic layers combined, dried (MgSO₄) and concentrated to yield 0.40 g. (90%) of 5-phenylpentan-2-ol, $[alpha]_D^{25} = -7.16°$ (CHCl₃).

PREPARATION 14

5-Phenyl-2S-pentanol

A sample of 9.9 g. (0.043 mole) of S(+)-propylene glycol 1-tosylate prepared from L-ethyl lactate according to Gombos et al., Chem. Ber. 109, p. 2145 (1976), was dissolved in 20 ml. of dry THF. This solution was added dropwise over 15 minutes to a rapidly stirred mixture of 98 ml. of 1.1M phenethyl magnesium bromide in THF (0.11 mole), immediately after 1.05 g. of cuprous chloride was added in one portion to the Grignard. The temperature of the initial cuprous chloride addition and of the subject tosylate addition was maintained at 18°–25° (upon the addition of the CuCl₂, the Grignard solution turned a deep purple). The reaction was then stirred for 1 hour at 25°, and quenched into 30 ml. of saturated NH₄Cl solution. The aqueous phase was separated and extracted 2× with 100 ml. portions of ethyl ether. The combined organic layer and washings were washed with brine (2×100 ml.), dried (MgSO₄) and concentrated to give 10.98 g. of crude title product as an oil. The pure S(+)-5-phenylpentan-2-ol was obtained by fractional high vacuum distillation. The purified S(+)-5-phenylpentan-2-ol had $[alpha]_D^{25} = +7.94$ (CHCl₃).

Other appropriate Grignard reagents are substituted for phenylethyl magnesium bromide to prepare a wide variety of other optically active alcohols useful in the present invention. Exemplary are:
4-phenyl-2S-butanol;
6-phenyl-2S-hexanol; and
2S-octanol.

PREPARATION 15

3-Bromo-5-(2-undecyl)anisole

3-Amino-5-(2-undecyl)anisole, prepared according to methods set forth by Johnson, U.S. Pat. No. 4,260,764 is diazotized and converted to the title compound according to procedures set forth by Bigelow, Org. Syntheses, Coll. Vol. I, pp. 135–137 (1941).

In the same manner, other aminoanisoles, also prepared by methods set forth by Johnson, are converted to:
3-bromo-5-(2-hexyl)anisole;
3-bromo-5-(3-ethyl-1-pentyl)anisole;
3-bromo-5-(5-phenyl-1-hexyl)anisole;
3-bromo-5-(6-phenyl-2-hexyl)anisole;
3-bromo-5-(6-phenyl-3-hexyl)anisole;
3-bromo-5-[6-(4-chlorophenyl)-2-hexyl]anisole;
3-bromo-5-[5-(4-fluorophenyl)-2-pentyl]anisole;
3-bromo-5-[6-(4-pyridyl)-2-hexyl]anisole;
3-bromo-5-[1-(1-heptyloxy)-2-propyl]anisole; and
3-bromo-5-[2-(2-phenylethoxy)-1-propyl]anisole.

PREPARATION 16

3-Methoxy-5-(2-undecyl)benzonitrile

3-Amino-5-(2-undecyl)anisole is diazotized and reacted with cuprous cyanide according to procedures set forth by Clarke and Read, Org. Syntheses, Coll. Vol. I, pp. 514–516 (1941) to produce the title product.

In the same manner other appropriate aminophenols are converted to:
3-methoxy-5-(5-phenyl-2-methyl-1-pentyl)benzonitrile;
3-methoxy-5-[5-(2-chlorophenyl)-1-hexyl]benzonitrile;
3-methoxy-5-[7-(3-fluorophenyl)-3-heptyl]benzonitrile; and
3-methoxy-5-[8-(3-pyridyl)-1-octyl]benzonitrile.

PREPARATION 17

3-Methoxy-5-(2-undecyl)benzoic Acid

The title nitrile of the preceding Preparation is hydrolyzed in methanol containing 0.5 ml. of 1N sodium hydroxide at room temperature for 5 hours to the title acid.

By the same method, the other nitriles of the preceding Preparation are converted to:
3-methoxy-5-(5-phenyl-2-methyl-1-pentyl)benzoic acid;
3-methoxy-5-[5-(2-chlorophenyl)-1-hexyl]benzoic acid;
3-methoxy-5-[7-(3-fluorophenyl)-3-heptyl]benzoic acid; and
3-methoxy-5-[8-(3-pyridyl)-1-octyl]benzoic acid.

If desired, the 3-methoxy-5-(2-undecyl)benzoic acid is resolved into its enantiomeric forms via salt formation with an optically active base, as set forth by Feiser and Fieser, Reagents for Organic Syntheses, John Wiley and Sons, 1967, pp. 977–978, thus affording:
3-methoxy-5-(2S-undecyl)benzoic acid; and
3-methoxy-5-(2R-undecyl)benzoic acid.

In the like manner, 3-methoxy-5-(5-phenyl-2-methyl-1-pentyl)benzoic acid is resolved to yield:
3-methoxy-5-(5-phenyl-2S-methyl-1-pentyl)benzoic acid; and
3-methoxy-5-(5-phenyl-2R-methyl-1-pentyl)benzoic acid.

PREPARATION 18

3-Methoxy-5-(2-undecyl)benzoyl Chloride

The title acid of the preceding Preparation is reacted with excess thionyl chloride in methylene chloride diluent in the presence of a trace of dimethylformamide. After refluxing for 3 hours the acid chloride is recovered by evaporation of the solvent and excess thionyl chloride chased with toluene.

By the same method, the other acids of the preceding Preparation are converted to:
3-methoxy-5-(5-phenyl-2-methyl-1-pentyl)benzoyl chloride;
3-methoxy-5-[5-(2-chlorophenyl)-1-hexyl]benzoyl chloride;
3-methoxy-5-[7-(3-fluorophenyl)-3-heptyl]benzoyl chloride;
3-methoxy-5-[8-(3-pyridyl)-1-octyl]benzoyl chloride;
3-methoxy-5-(2S-undecyl)benzoyl chloride;
3-methoxy-5-(2R-undecyl)benzoyl chloride;
3-methoxy-5-(5-phenyl-2S-methyl-1-pentyl)benzoyl chloride; and
3-methoxy-5-(5-phenyl-2R-methyl-1-pentyl)benzoyl chloride.

PREPARATION 19

3-Methoxy-5-(2-undecyl)benzaldehyde

Method A

The title acid chloride of the preceding Preparation is subjected to hydrogenation under Rosenmund conditions, as set forth by Mosettig and Mozingo in Organic Reactions, Vol. 4, John Wiley and Sons, New York, 1948, pp. 362–377, producing the title product.

Method B

The title nitrile of Preparation 16 is subjected to the Stephen reduction under conditions set forth by Williams, Org. Syntheses, Coll. Vol. III, pp. 626–627 (1955).

Method C

The title acid chloride of the preceding Preparation is reacted with excess ethyl mercaptan to yield the correspnding thiol ester. Hydrogenolysis to the title aldehyde is effected by refluxing the thiol ester with Raney nickel in ethanol under conditions set forth by Wolfrom and Karbinos, J. Am. Chem. Soc. 68, pp. 1455–1456 (1946).

Method D

3-Methoxy-5-(2-undecyl)benzyl bromide is oxidized according to methods set forth by Kornblum et al., J. Am. Chem. Soc. 81, pp. 4113–4114 (1959). The required benzyl bromide is prepared according to methods set forth by Althuis et al., U.S. Pat. No. 4,188,495.

Method E

3-Bromo-5-(2-undecyl)anisole is reacted with magnesium in ether to form the corresponding Grignard reagent, then reacted with ethyl orthoformate and hydrolyzed to title product according to procedures set forth by Smith and Nichols, J. Org. Chem. 6, pp. 489–506 (1941).

By methods A-D, the appropriate acid chlorides, nitriles or bromomethyl compounds are converted to:
3-methoxy-5-(5-phenyl-2-methyl-1-pentyl)benzaldehyde;
3-methoxy-5-[5-(2-chlorophenyl)-1-hexyl]benzaldehyde;
3-methoxy-5-[7-(3-fluorophenyl)-3-heptyl]benzaldehyde;
3-methoxy-5-[8-(3-pyridyl)-1-octyl]benzaldehyde;
3-methoxy-5-(2S-undecyl)benzaldehyde;
3-methoxy-5-(2R-undecyl)benzaldehyde;
3-methoxy-5-(5-phenyl-2S-methyl-1-pentyl)benzaldehyde; and
3-methoxy-5-(5-phenyl-2R-methyl-1-pentyl)benzaldehyde.

By method E, aryl bromides from an earlier Preparation are converted to:
3-hydroxy-5-(2-hexyl)benzaldehyde;
3-hydroxy-5-(3-ethyl-1-pentyl)benzaldehyde;
3-hydroxy-5-(5-phenyl-1-hexyl)benzaldehyde;
3-hydroxy-5-(6-phenyl-2-hexyl)benzaldehyde;
3-hydroxy-5-[6-(4-chlorophenyl)-2-hexyl]benzaldehyde;
3-hydroxy-5-[6-(4-fluorophenyl)-2-pentyl]benzaldehyde;
3-hydroxy-5-[6-(4-pyridyl)-2-hexyl]benzaldehyde;
3-hydroxy-5-[1-heptyloxy)-2-propyl]benzaldehyde; and
3-bromo-5-[2-(2-phenylethoxy)-1-propyl]benzaldehyde.

PREPARATION 20

Benzyl Methanesulfonate

Under nitrogen methylene chloride (1.4 liter), benzyl alcohol (129.6 g., 1.2 moles) and triethylamine (182 g., 1.8 moles) were combined, stirred and cooled to $-5°$ C. in an ice-water-acetone bath. A solution of methanesulfonyl chloride (150 g., 1.31 moles) in 100 ml. of methylene chloride was added over 49 minutes, maintaining the temperature between $-5°$ and $2°$ C. After stirring for 10 minutes at $0°-2°$ C., the reaction was diluted with 500 ml. of water, precooled to $5°$ C. The organic layer was separated, washed $2 \times 500$ ml. of cold water, dried over $MgSO_4$, filtered and evaporated in vacuo to yield title product as a light yellow oil [190 g.; 85%; $^1$H-NMR ($CDCl_3$) delta (ppm): 2.9 (s, 3H), 5.2 (s, 2H), 7.4 (m, 5H); $R_f$ 0.75 ($CH_2Cl_2$)]. This product was refrigerated until used in the next step.

PREPARATION 21

Ethyl 2S-Benzyloxypropionate

Under nitrogen, benzyl methanesulfonate (181.5 g., 0.975 mole) was combined and stirred with S ethyl lactate (ethyl 2S-hydroxypropionate; 393 g., 3.33 moles) and the resulting solution heated on a steam bath to $94°$ C. over 15 minutes and held for 1.5 hours at this temperature. The reaction mixture was cooled to $45°$ C., poured into 2 liters of cold toluene. Water (500 ml.) was added and the mixture stirred for 5 minutes. The aqueous phase was separated and extracted with 200 ml. fresh toluene. The organic layers were combined, washed in sequence $2 \times 500$ ml. $H_2O$, $1 \times 500$ ml. saturated $NaHCO_3$, $2 \times 500$ ml. water and $1 \times 500$ ml. saturated NaCl, dried over $MgSO_4$, filtered, and evaporated in vacuo to yield crude product as an oil [228 g., 112% [alpha]$_D^{25}$ $-60.8°$, C=1.11 ($CHCl_3$)], which $^1$H-NMR indicated to be contaminated with ethyl lactate. Distillation in vacuo gave, after an early boiling solvent fraction 1 [25 ml., b.p. to $79°$ C./1.2 mm., [alpha]$_d$ $-6.9°$, C=1.13 ($CHCl_3$)]; fractions 2-8 [74 ml., b.p. $82°$ C./1.3 mm to $114°$ C./3 mm.; [alpha]$_D$ $-42.1°$ to $-76.2°$, C=1.09-1.16 ($CHCl_3$)] as a mixture of S ethyl lactate and title product; and fractions 9-12 [57 ml.; b.p. $115°$ C./3 mm., $98°-100°/0.75$ mm., $102°-106°$ C./1.0 mm.; [alpha]$_D$ $-80.0°$ to $-83.7°$, C=1.01-1.17 ($CHCl_3$)] of substantially pure title product. A higher boiling pot residue of 49 g. remained. A portion of fraction 10 (3g.) was voided of traces of ethyl lactate by taking up in 100 ml. of hexane and equilibrating with 30 ml. $H_2O$. The hexane layer was separated, washed $3 \times 30$ ml. $H_2O$, dried over $MgSO_4$, filtered and concentrated to an oil [2.4 g.; $R_f$ 0.32 (6:1 hexane:ethyl acetate); [alpha]$_D^{25}$ $-83.3°$, C=1.13 ($CHCl_3$)].

PREPARATION 22

2S-Benzyloxy-1-propanol

Fractions 2-9 and 12 from the above distillation (106.1 g. total weight, 0.45 moles of ethyl 2S-benzyloxypropionate and 0.25 moles of S ethyl lactate) was dissolved in 100 ml. of anhydrous ethanol and the solution added dropwise to a stirred mixture of $NaBH_4$ (37.85 g., 1.0 mole) and 500 ml. of anhydrous ethanol under nitrogen over a one hour period. The temperature was maintained at $25°-30°$ C. during addition by cooling with a $20°$ C. water bath. After stirring for 20 hours at ambient temperature, the reaction mixture was cooled to $10°$ C. and 95 ml. of 12N HCl (1.14 mole) added dropwise over 15 minutes under a sweep of nitrogen. The resulting slurry was filtered with 100 ml. ethanol wash. The filtrate and wash were combined and concentrated in vacuo to 150 ml. The concentrate was diluted with 200 ml. of water and 300 ml. of ethyl acetate, the pH was adjusted from 1.5 to 9.0 with 50 ml. of 4N NaOH (causing precipitated solids to dissolve) and the layers were separated. The aqueous phase was washed $1 \times 100$ ml. and then $1 \times 50$ ml. of ethyl acetate. The three organic layers were combined, washed $2 \times 150$ ml. $H_2O$ and then $1 \times 150$ ml. saturated NaCl, dried over $MgSO_4$, filtered, and evaporated to yield title product as an oil [50.5 g.; [alpha]$_D^{25}$ $+47.9$, C=1.08 ($CHCl_3$); $+27.736$ (neat); $R_f$ 0.1 ($CH_2Cl_2$)].

PREPARATION 23

2S-Benzyloxy-1-propyl Mesylate

Under nitrogen, 2S-benzyloxy-1-propanol (49.8 g., 0.3 mole), 400 ml. of $CH_2Cl_2$ and triethylamine (40.5 g., 0.4 mole) were combined, stirred and cooled to $-5°$ C. in an ice-water-acetone bath. Maintaining $-5°$ C., methanesulfonyl chloride (37.8 g., 0.33 mole) in 30 ml. $CH_2Cl_2$ was added over one hour. After stirring at $-5°$ C. for 0.5 hour, $H_2O$ (200 ml. at $5°$ C.) was added. The layers were separated and the aqueous layer washed $1 \times 100$ ml. $CH_2Cl_2$. The combined organic layers were washed in sequence $1 \times 100$ ml. $H_2O$, $1 \times 100$ ml. 1N HCl, $1 \times 100$ ml. $H_2$), $1 \times 100$ ml. saturated $NaHCO_3$ and $1 \times 100$ ml. $H_2O$, dried over $MgSO_4$, filtered, and concentrated in vacuo to yield title product as an oil [72.2 g., 98.5%; [alpha]$_D^{25}$ $+7.7$, C=1.00 ($CHCl_3$); $R_f$ 0.6 ($CH_2Cl_2$)].

PREPARATION 24

2S-Benzyloxy-propyl Iodide

Under nitrogen with stirring, sodium iodide (90 g., 0.6 mole) was dissolved in one liter dry acetone. At $32°$ C., 2S-benzyloxy-1-propyl mesylate (71.5 g., 0.293 mole) was added. The reaction mixture was warmed to 59°-60° C. (gentle reflux) and held for 20 hours, at which time tlc indicated about 20% starting material to remain. Additional sodium iodide (30 g., 0.2 mole) was added and refluxing continued for 3 hours. The reaction was cooled to room temperature and filtered with acetone wash. The combined filtrate and wash was concentrated to 150 ml. of oily solids, diluted with 300 ml. toluene and 200 ml. H$_2$O, the layers separated and the aqueous phase extracted 2×100 ml. toluene. The three organic layers were combined, washed 2×200 ml. H$_2$O, dried over MgSO$_4$, filtered and evaporated to yield title product as an oil [79 g., 96%; [alpha]$_D$=+8.0°, C=1.08 (CHCl$_3$), $^1$H-NMR (CDCl$_3$) delta (ppm): 1.4 (d, 3H), 3-3.6 (m, 3H), 4.6 (s, 2H), 7.35 (s, 5H)].

PREPARATION 25

Ethyl 2-Benzoyl-4S-benzyloxyvalerate

Under nitrogen, sodium hydride (50% in oil, 13.6 g., 0.283 mole) was washed with 3×200 ml. of dry hexane. To the resulting hexane wet NaH, 130 ml. dimethylformamide was added, followed by the dropwise addition of ethyl benzoylacetate (54.4 g., 0.283 mole) over 45 minutes, maintaining the temperature 28°-32° C. with a 10° C. water bath and sweeping away evolved H$_2$ with N$_2$. After stirring for 85 minutes at 25° C., 2S-benzyloxy-1-propyl iodide (78 g., 0.283 mole) was added with 40 ml. of dimethylformamide for rinse. The reaction mixture was then heated and stirred at 122°-126° C. for 2 hours (during which solids precipitated), cooled to 70° C., diluted with 350 ml. toluene and 560 ml. of ice water, and the resulting layers separated. The aqueous layer was extracted 3×150 ml. toluene. The four organic layers were combined, washed 3×150 ml. H$_2$O and then 1×150 ml. saturated NaCl, dried over MgSO$_4$, filtered and concentrated in vacuo to yield title product as an oil (90 g., 94%; [alpha]$_D^{25}$+15.8°, C=1.12 (CHCl$_3$); R$_f$ 0.35 (6:1 hexane:ethyl acetate)].

Substitution of an equivalent amount of S-propylene oxide for 2S-benzyl-1-propyl iodide in this process and operating in a closed container (i.e. under pressure) to avoid loss of the volatile epoxide affords a method for the preparation of ethyl 2-benzoyl-4S-hydroxyvalerate.

PREPARATION 26

4S-Benzyloxy-1-phenyl-1-pentanone

Ethyl 2-benzoyl-4S-benzyloxyvalerate (89 g., 0.26 mole), ethanol (175 ml.), water (175 ml.) and KOH (85%, 51 g., 0.8 mole) were combined with stirring under nitrogen during which the temperature rose to 45° C. The reaction mixture was heated to 79° C. under a reflux condenser and held for 18 hours. The reaction mixture was cooled to 25° C., diluted with 350 ml. of water and 300 ml. of toluene, the layers separated, and the aqueous layer washed 1×200 ml. and 2×150 ml. toluene. The organic layers were combined, washed 2×200 ml. H$_2$O and 1×200 ml. saturated NaCl, dried over MgSO$_4$, filtered and concentrated in vacuo to yield title product as an oil [45.5 g., 65%; [alpha]$_D^{25}$+21.92°, C=1.20 (CHCl$_3$); R$_f$ 0.55 (6:1 hexane:ethyl acetate)].

The same method is used to convert ethyl 2-benzoyl-4S-hydroxyvalerate to 4S-hydroxy-1-phenyl-1-pentanone.

PREPARATION 27

5-Phenyl-2S-pentanol

4S-Benzyloxy-1-phenyl-1-pentanone (45 g., 0.168 mole) in 150 ml. of toluene, 15 ml. of absolute alcohol and 3 drops concentrated HCl were hydrogenated over 4 g. 50% water wet 5% Pd/C at 50-60 psig and 25° C. After hydrogenating for 6 hours, an additional 4 g. catalyst was charged and hydrogenation continued for 2.5 hours, by which time three equivalents of hydrogen were consumed and there had been no uptake over the final 1.5 hour period. The catalyst was recovered by filtration. The filtrate was neutralized by stirring over a 5 cc volume of solid NaHCO$_3$, dried over MgSO$_4$, filtered and concentrated in vacuo to yield title product as an oil [22 g., 80%; [alpha]$_D^{25}$+8.63, C=1.02 (CHCl$_3$); R$_f$ 0.2 (6:1 hexane:ethyl acetate)]. If desired the title product was further purified by simple distillation to remove traces of tlc origin material, b.p. 90-94/0.7 mm. with nearly quantitative recovery.

By the same procedure, with uptake of two rather than three equivalents of hydrogen, 4S-hydroxy-1-phenyl-1-pentanone is converted to 5-phenyl-2S-pentanol.

We claim:

1. A compound having the formula

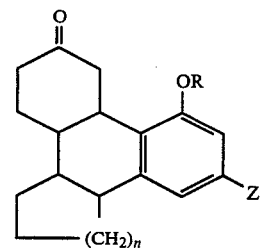

wherein n is 1 to 2;

R is H, benzoyl, (C$_1$-C$_5$)alkanoyl or —CO(CH$_2$)$_m$Y, wherein m is 1, 2, 3 or 4, Y is —COOH, or —NR'R", R' and R" when taken separately are each independently H or (C$_1$-C$_4$)alkyl, and R' and R" when taken together with the nitrogen to which they are attached are piperidino, pyrrolo, pyrrolidino, morpholino or N-[(C$_1$-C$_4$)alkyl]-piperazino; and Z is (C$_5$-C$_{13}$)alkyl, (C$_5$-C$_{13}$)alkoxy, (C$_5$-C$_{13}$)alkoxyalkyl, (C$_8$-C$_{13}$)pyridylalkyl, (C$_8$-C$_{13}$)pyridylalkoxy, (C$_8$-C$_{13}$)pyridyloxyalkyl, (C$_8$-C$_{13}$)pyridylalkoxyalkyl, (C$_9$-C$_{14}$)phenylalkyl, (C$_9$-C$_{14}$)phenylalkoxy, (C$_9$-C$_{14}$)phenoxyalkyl, or (C$_9$-C$_{14}$)phenylalkoxyalkyl, wherein said phenyl groups are optionally substituted with a chloro or a fluoro;

a pharmaceutically-acceptable acid addition salt thereof when R is —CO(CH$_2$)$_m$Y and Y is —NR'R"; or a pharmaceutically-acceptable cationic salt thereof when R is —CO(CH$_2$)$_m$Y and Y is —COOH.

2. A compound of claim 1 having the absolute or relative stereochemical formula

3. A compound of claim 2 having the absolute or relative stereochemical formula
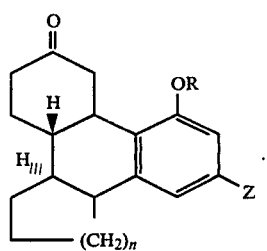
4. A compound of claim 3 having the absolute stereochemical formula
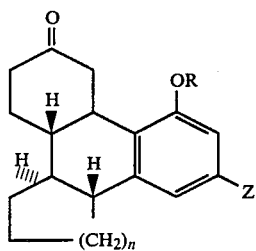
5. A compound of any one of claims 1, 2, 3 or 4 wherein Z is 5-phenyl-2-pentyloxy.
6. A compound having the formula:
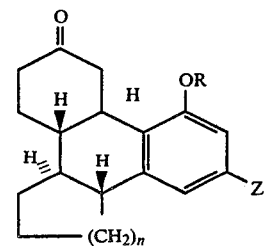
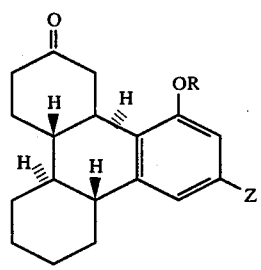
wherein R is acetyl and Z is 5-phenyl-2-pentyloxy.
7. A compound of claim 6 wherein Z is 5-phenyl-2R-pentyloxy.
* * * * *